United States Patent [19]
Frye et al.

[11] Patent Number: 6,008,041
[45] Date of Patent: *Dec. 28, 1999

[54] BOVINE DIPEPTIDYLAMINOPEPTIDASE 1

[75] Inventors: Christopher Carl Frye, Bloomington; Charles Lee Hershberger, Greenfield, both of Ind.; Haichao Zhang, Lake Bluff, Ill.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/850,227

[22] Filed: May 2, 1997

Related U.S. Application Data

[60] Provisional application No. 60/017,644, May 8, 1996.
[51] Int. Cl.⁶ .............. C12N 9/50; C12N 5/00; C12N 1/20; C07H 21/04
[52] U.S. Cl. ............ 435/325; 435/219; 435/252.3; 435/254.11; 435/320.1; 536/23.2
[58] Field of Search ............ 435/219, 252.3, 435/254.11, 320.1, 325; 536/23.2

[56] References Cited

PUBLICATIONS

Paris et al. (1995) Molecular Cloning and Sequence Analysis of Human Preprocathespin C. FEBS Lett. 396(2–3): 326–330.

K. Ishidoh, et al. "Molecular Cloning of cDNA for Rat Cathespin C" *The Journal of Biological Chemistry* 266(25): 16312–16317 (Sep. 5, 1991).

*Primary Examiner*—Lisa Hobbs
*Attorney, Agent, or Firm*—Paul R. Cantrell; Paul J. Gaylo

[57] ABSTRACT

The present invention provides the cDNA sequence encoding bovine dipeptidylaminopeptidase 1. The invention demonstrates that bovine DAP 1 coded by a single cDNA. The mature protein is derived from a single polypeptide consisting of a signal peptide, and a major polypeptide which is processed to generate the a subunit, b subunit and g subunit.

7 Claims, No Drawings

BOVINE DIPEPTIDYLAMINOPEPTIDASE 1

PRIORITY CLAIM

This application claims the benefit of U.S. Provisional Patent Application 60/017,644, filed May 8, 1996.

BACKGROUND OF THE INVENTION

Dipeptidylaminopeptidase I (DAP 1) (EC 3.4.14.1), or cathepsin C, has long been investigated in term of its purification, kinetic mechanism, and physiological roles. It is a member of a group of lysosomal cysteine proteases involved in protein degradation. It is a dipeptidylaminopeptidase which removes N-terminal dipeptides sequentially from an unsubstituted N-terminal peptide or protein with broad substrate specificity. It has been postulated to function in protein turnover. DAP 1 absence/overproduction has been proposed to be involved in Duchenne muscular dystrophy. C. N. Pato, et. al., *Proceedings of the National Academy of Sciences, U.S.A.*, 80:4732–4736 (1983). DAP 1 has been demonstrated to be present in elevated levels in cytotoxic lymphocytes. D. L. Thiele and P. E. Lipsky, *Proceedings of the National Academy of Sciences, U.S.A.*, 87:83–87 (1990).

DAP 1 has been isolated from a variety of sources including bovine spleen [R. M. Metrione, et. al., *Biochemistry*, vol. 5 (1990)], bovine pituitary [J. K. McDonald, et. al., *Journal of Biological Chemistry*, 241:1494–1501 (1966)], rat liver [F. L. Huang and A. L. Tappel, *Biochimica et Biophysica Acta*, 268:527–538 (1972)] and human spleen [M. McGuire, et al., *Archives of Biochemica et Biophysica*, 295:280–288 (1992)]. It consists of several polypeptides in a complexed oligomeric structure. R. M. Metrione, et al., *Biochemistry*, vol. 9 no. 12.

In the case of bovine spleen DAP 1, the purified enzyme has three distinctive subunits: 23 kD (a chain), 21 kD (b chain), 5.6 kD (g chain), forming an oligomeric structure of a4b4g4. It has been reported that the subunits of rat DAPI may be derived from a single precursor as evidence in rat cell lines (F. Mainferme, et al., *European Journal of Biochemistry*, 153: 211–216 (1985); and V. Burge, et al., *Biochemistry Journal*, 275:707–800 (1991). Recent cloning experiments have confirmed that the oligomeric protein is actually a proteolytic product of a single polypeptide. K. Ishidoh, et al., *Journal of Biological Chemistry*, 266:16312–16317 (1991).

In addition to bovine dipeptidylaminopeptidase 1 described in the publications above, another dipeptidylaminopeptidase frequently employed in the processing of recombinant proteins is that derived from the slime mold *Dictyostelium discoidium*. The synthesis, purification and use of this protease, often abbreviated as dDAP, are described in European Patent Publication 595,476, published May 4, 1994, and U.S. patent application Nos. 08/301,519, filed Sep. 7, 1994, and 08/445,308, filed May 19, 1995, all of which are herein incorporated by reference.

Bovine DAP 1 has several unique properties. First, it is a thiolproteinase instead of being a serine proteinase as is a class of dipeptidylaminopeptidases, such as DAPII, DAPIII, and DAPIV. Second, it functions as a dipeptidylaminopeptidase in a thiolproteinase family which are endopeptidases. Third, it strongly requires Cl⁻ for maximal activity and is mildly heat resistant. J. Gorter and M. Gruber, *Biochimica et Biophysica Acta*, 198:546–555 (1970). The enzyme is beginning to become one of the major bioprocessing enzymes used in industry.

Until the present invention, it was not known whether the cDNA sequence encoding bovine DAP 1 consisted of three independent cDNAs or was encoded in by a single cDNA. The present invention demonstrates that bovine DAP 1 is encoded by a single cDNA. Due to the increasing importance of avoiding infectious agents, be they viruses or prions, arising from animal sourced material, the pharmaceutical industry has favored the use of non-animal sourced enzymes in the biosynthetic processing of pharmaceutical proteins. Recombinant expression of such enzymes has thus been favored. It is, therefore, advantageous to have a cloned source for the enzyme.

SUMMARY OF THE INVENTION

The present invention provides the cDNA sequence encoding bovine dipeptidylaminopeptidase 1. The invention demonstrates that bovine DAP 1 coded by a single cDNA. The mature protein is derived from a single polypeptide consisting of a signal peptide, and a major polypeptide which is processed to generate the a subunit, b subunit and g subunit.

This invention also encompasses nucleic acids, both RNA and DNA which encode the bovine dipeptidylaminopeptidase 1 of SEQ ID NO:2. Specifically, this invention encompasses nucleic acid compounds comprising the following sequences

```
GAC ACG CCT GCC AAC TGC ACC TAC CCC GAC CTG CTG GGC ACC TGG GTC    48
Asp Thr Pro Ala Asn Cys Thr Tyr Pro Asp Leu Leu Gly Thr Trp Val
 1               5                  10                  15

TTC CAG GTG GGC TCC AGC GGC TCC CAG CGC CAT GTC AAC TGC TCG GTG    96
Phe Gln Val Gly Ser Ser Gly Ser Gln Arg His Val Asn Cys Ser Val
                20                  25                  30

ATG GGA CCC CCA GAA AAA AAA GTG GTG GTG CAC CTC AAG AAG TTG GAT   144
Met Gly Pro Pro Glu Lys Lys Val Val Val His Leu Lys Lys Leu Asp
            35                  40                  45

ACA GCA TAT GAT GAC TTT GGC AAT TCC GGC CAT TTC ACC ATC ATT TAC   192
Thr Ala Tyr Asp Asp Phe Gly Asn Ser Gly His Phe Thr Ile Ile Tyr
        50                  55                  60

AAT CAA GGC TTT GAG ATT GTG TTG AAT GAC TAC AAG TGG TTC GCC TTT   240
Asn Gln Gly Phe Glu Ile Val Leu Asn Asp Tyr Lys Trp Phe Ala Phe
 65                  70                  75                  80

TTT AAG TAT AAA GAA GAG GGT GGC AAG GTA ACC AGT TAC TGC CAC GAG   288
Phe Lys Tyr Lys Glu Glu Gly Gly Lys Val Thr Ser Tyr Cys His Glu
                85                  90                  95
```

```
ACC ATG ACT GGC TGG GTC CAT GAC GTG CTG GGC CGG AAC TGG GCC TGT    336
Thr Met Thr Gly Trp Val His Asp Val Leu Gly Arg Asn Trp Ala Cys
            100                 105                 110

TTC ACT GGA AGG AAG ACA GGA AAT ACC TCG GAG AAC GTG AAC GTG AAC    384
Phe Thr Gly Arg Lys Thr Gly Asn Thr Ser Glu Asn Val Asn Val Asn
            115                 120                 125

ACA GCA CGC CTT GCG GGT CTC GAG GAA ACG TAT TCT AAT AGG CTC TAC    432
Thr Ala Arg Leu Ala Gly Leu Glu Glu Thr Tyr Ser Asn Arg Leu Tyr
            130                 135                 140

AGA TAT AAC CAT GAC TTT GTG AAA GCT ATC AAT GCC ATT CAG AAG TCT    480
Arg Tyr Asn His Asp Phe Val Lys Ala Ile Asn Ala Ile Gln Lys Ser
145                 150                 155                 160

TGG ACT GCA GCC CCA TAC ATG GAA TAT GAG ACT CTT ACC CTA AAA GAG    528
Trp Thr Ala Ala Pro Tyr Met Glu Tyr Glu Thr Leu Thr Leu Lys Glu
                165                 170                 175

ATG ATT AGG AGA GGT GGT GGC CAT AGC CGG AGA ATT CCA AGG CCC AAA    576
Met Ile Arg Arg Gly Gly Gly His Ser Arg Arg Ile Pro Arg Pro Lys
            180                 185                 190

CCT GCA CCA ATC ACT GCT GAA ATA CAG AAA AAG ATT TTG CAT TTG CCA    624
Pro Ala Pro Ile Thr Ala Glu Ile Gln Lys Lys Ile Leu His Leu Pro
            195                 200                 205

ACA TCC TGG GAT TGG AGA AAC GTT CAT GGT ATC AAT TTT GTT ACT CCT    672
Thr Ser Trp Asp Trp Arg Asn Val His Gly Ile Asn Phe Val Thr Pro
            210                 215                 220

GTT CGA AAC CAA GGG TCT TGT GGA AGC TGC TAC TCA TTT GCT TCT ATG    720
Val Arg Asn Gln Gly Ser Cys Gly Ser Cys Tyr Ser Phe Ala Ser Met
225                 230                 235                 240

GGG ATG ATG GAA GCA AGA ATC CGC ATA CTA ACC AAC AAC ACT CAG ACC    768
Gly Met Met Glu Ala Arg Ile Arg Ile Leu Thr Asn Asn Thr Gln Thr
                245                 250                 255

CCG ATC TTG AGT CCT CAG CAG GTT GTG TCT TGC AGT CAG TAT GCT CAA    816
Pro Ile Leu Ser Pro Gln Gln Val Val Ser Cys Ser Gln Tyr Ala Gln
            260                 265                 270

GGC TGT GAA GGT GGC TTC CCT TAC CTC ATC GCA GGG AAG TAT GCC CAG    864
Gly Cys Glu Gly Gly Phe Pro Tyr Leu Ile Ala Gly Lys Tyr Ala Gln
            275                 280                 285

GAC TTT GGG TTG GTG GAA GAG GAC TGT TTC CCC TAC ACA GGC ACG GAT    912
Asp Phe Gly Leu Val Glu Glu Asp Cys Phe Pro Tyr Thr Gly Thr Asp
            290                 295                 300

TCG CCG TGC AGA CTG AAA GAG GGC TGC TTC CGG TAC TAT TCC TCC GAG    960
Ser Pro Cys Arg Leu Lys Glu Gly Cys Phe Arg Tyr Tyr Ser Ser Glu
305                 310                 315                 320

TAC CAC TAC GTG GGC GGT TTC TAC GGG GGC TGC AAT GAA GCC CTG ATG   1008
Tyr His Tyr Val Gly Gly Phe Tyr Gly Gly Cys Asn Glu Ala Leu Met
                325                 330                 335

AAG CTT GAG CTG GTC CAT CAG GGG CCC ATG GCC GTC GCC TTT GAA GTC   1056
Lys Leu Glu Leu Val His Gln Gly Pro Met Ala Val Ala Phe Glu Val
            340                 345                 350

TAC GAC GAC TTC CTC CAC TAC CGC AAG GGC GTC TAC CAC CAC ACG GGG   1104
Tyr Asp Asp Phe Leu His Tyr Arg Lys Gly Val Tyr His His Thr Gly
            355                 360                 365

CTG CGA GAC CCT TTC AAC CCC TTC GAG CTG ACC AAT CAT GCT GTG CTG   1152
Leu Arg Asp Pro Phe Asn Pro Phe Glu Leu Thr Asn His Ala Val Leu
            370                 375                 380

CTG GTG GGC TAT GGC ACT GAC GCG GCC TCT GGA CTG GAT TAC TGG ATT   1200
Leu Val Gly Tyr Gly Thr Asp Ala Ala Ser Gly Leu Asp Tyr Trp Ile
385                 390                 395                 400

GTT AAA AAC AGC TGG GGC ACC AGC TGG GGT GAG AAC GGT TAC TTC CGC   1248
Val Lys Asn Ser Trp Gly Thr Ser Trp Gly Glu Asn Gly Tyr Phe Arg
                405                 410                 415
```

```
ATC CGC AGA GGA ACC GAC GAG TGT GCG ATC GAA AGC ATA GCG CTG GCG   1296
Ile Arg Arg Gly Thr Asp Glu Cys Ala Ile Glu Ser Ile Ala Leu Ala
            420                 425                 430

GCC ACC CCG ATT CCT AAG TTG                                      1317
Ala Thr Pro Ile Pro Lys Leu
        435
``` hereinafter referred to as SEQ ID NO:1;

```
ATG GGT CCC TGG TCC GGC TCG CGG CTC GTC GCT CTC TTG CTG CTC GTC    48
Met Gly Pro Trp Ser Gly Ser Arg Leu Val Ala Leu Leu Leu Leu Val
440                 445                 450                 455

TAT GGC GCT GGC TCC GTG CGC GGG GAC ACG CCT GCC AAC TGC ACC TAC    96
Tyr Gly Ala Gly Ser Val Arg Gly Asp Thr Pro Ala Asn Cys Thr Tyr
                    460                 465                 470

CCC GAC CTG CTG GGC ACC TGG GTC TTC CAG GTG GGC TCC AGC GGC TCC   144
Pro Asp Leu Leu Gly Thr Trp Val Phe Gln Val Gly Ser Ser Gly Ser
                475                 480                 485

CAG CGC GAT GTC AAC TGC TCG GTG ATG GGA CCC CCA GAA AAA AAA GTG   192
Gln Arg Asp Val Asn Cys Ser Val Met Gly Pro Pro Glu Lys Lys Val
            490                 495                 500

GTG GTG CAC CTC AAG AAG TTG GAT ACA GCA TAT GAT GAC TTT GGC AAT   240
Val Val His Leu Lys Lys Leu Asp Thr Ala Tyr Asp Asp Phe Gly Asn
        505                 510                 515

TCC GGC CAT TTC ACC ATC ATT TAC AAT CAA GGC TTT GAG ATT GTG TTG   288
Ser Gly His Phe Thr Ile Ile Tyr Asn Gln Gly Phe Glu Ile Val Leu
520                 525                 530                 535

AAT GAC TAC AAG TGG TTC GCC TTT TTT AAG TAT AAA GAA GAG GGT GGC   336
Asn Asp Tyr Lys Trp Phe Ala Phe Phe Lys Tyr Lys Glu Glu Gly Gly
                    540                 545                 550

AAG GTA ACC AGT TAC TGC CAC GAG ACC ATG ACT GGC TGG GTC CAT GAC   384
Lys Val Thr Ser Tyr Cys His Glu Thr Met Thr Gly Trp Val His Asp
                555                 560                 565

GTG CTG GGC CGG AAC TGG GCC TGT TTC ACT GGA AGG AAG ACA GGA AAT   432
Val Leu Gly Arg Asn Trp Ala Cys Phe Thr Gly Arg Lys Thr Gly Asn
            570                 575                 580

ACC TCG GAG AAC GTG AAC GTG AAC ACA GCA CGC CTT GCG GGT CTC GAG   480
Thr Ser Glu Asn Val Asn Val Asn Thr Ala Arg Leu Ala Gly Leu Glu
        585                 590                 595

GAA ACG TAT TCT AAT AGG CTC TAC AGA TAT AAC CAT GAC TTT GTG AAA   528
Glu Thr Tyr Ser Asn Arg Leu Tyr Arg Tyr Asn His Asp Phe Val Lys
600                 605                 610                 615

GCT ATC AAT GCC ATT CAG AAG TCT TGG ACT GCA GCC CCA TAC ATG GAA   576
Ala Ile Asn Ala Ile Gln Lys Ser Trp Thr Ala Ala Pro Tyr Met Glu
                    620                 625                 630

TAT GAG ACT CTT ACC CTA AAA GAG ATG ATT AGG AGA GGT GGT GGC CAT   624
Tyr Glu Thr Leu Thr Leu Lys Glu Met Ile Arg Arg Gly Gly Gly His
                635                 640                 645

AGC CGG AGA ATT CCA AGG CCC AAA CCT GCA CCA ATC ACT GCT GAA ATA   672
Ser Arg Arg Ile Pro Arg Pro Lys Pro Ala Pro Ile Thr Ala Glu Ile
            650                 655                 660

CAG AAA AAG ATT TTG CAT TTG CCA ACA TCC TGG GAT TGG AGA AAC GTT   720
Gln Lys Lys Ile Leu His Leu Pro Thr Ser Trp Asp Trp Arg Asn Val
        665                 670                 675

CAT GGT ATC AAT TTT GTT ACT CCT GTT CGA AAC CAA GGG TCT TGT GGA   768
His Gly Ile Asn Phe Val Thr Pro Val Arg Asn Gln Gly Ser Cys Gly
680                 685                 690                 695

AGC TGC TAC TCA TTT GCT TCT ATG GGG ATG ATG GAA GCA AGA ATC CGC   816
Ser Cys Tyr Ser Phe Ala Ser Met Gly Met Met Glu Ala Arg Ile Arg
                    700                 705                 710
```

```
ATA CTA ACC AAC AAC ACT CAG ACC CCG ATC TTG AGT CCT CAG GAG GTT    864
Ile Leu Thr Asn Asn Thr Gln Thr Pro Ile Leu Ser Pro Gln Glu Val
            715                 720                 725

GTG TCT TGC AGT CAG TAT GCT CAA GGC TGT GAA GGT GGC TTC CCT TAC    912
Val Ser Cys Ser Gln Tyr Ala Gln Gly Cys Glu Gly Gly Phe Pro Tyr
            730                 735                 740

CTC ATC GCA GGG AAG TAT GCC CAG GAC TTT GGG TTG GTG GAA GAG GAC    960
Leu Ile Ala Gly Lys Tyr Ala Gln Asp Phe Gly Leu Val Glu Glu Asp
            745                 750                 755

TGT TTC CCC TAC ACA GGC ACG GAT TCG CCG TGC AGA CTG AAA GAG GGC   1008
Cys Phe Pro Tyr Thr Gly Thr Asp Ser Pro Cys Arg Leu Lys Glu Gly
760                 765                 770                 775

TGC TTC CGG TAC TAT TCC TCC GAG TAC CAC TAC GTG GGC GGT TTC TAC   1056
Cys Phe Arg Tyr Tyr Ser Ser Glu Tyr His Tyr Val Gly Gly Phe Tyr
                    780                 785                 790

GGG GGC TGC AAT GAA GCC CTG ATG AAG CTT GAG CTG GTC CAT CAG GGG   1104
Gly Gly Cys Asn Glu Ala Leu Met Lys Leu Glu Leu Val His Gln Gly
            795                 800                 805

CCC ATG GCC GTC GCC TTT GAA GTC TAC GAC GAC TTC CTC CAC TAC CGC   1152
Pro Met Ala Val Ala Phe Glu Val Tyr Asp Asp Phe Leu His Tyr Arg
            810                 815                 820

AAG GGC GTC TAC CAC CAC ACG GGG CTG CGA GAC CCT TTC AAC CCC TTC   1200
Lys Gly Val Tyr His His Thr Gly Leu Arg Asp Pro Phe Asn Pro Phe
            825                 830                 835

GAG CTG ACC AAT CAT GCT GTG CTG CTG GTG GGC TAT GGC ACT GAC GCG   1248
Glu Leu Thr Asn His Ala Val Leu Leu Val Gly Tyr Gly Thr Asp Ala
840                 845                 850                 855

GCC TCT GGA CTG GAT TAC TGG ATT GTT AAA AAC AGC TGG GGC ACC AGC   1296
Ala Ser Gly Leu Asp Tyr Trp Ile Val Lys Asn Ser Trp Gly Thr Ser
                860                 865                 870

TGG GGT GAG AAC GGT TAC TTC CGC ATC CGC AGA GGA ACC GAC GAG TGT   1344
Trp Gly Glu Asn Gly Tyr Phe Arg Ile Arg Arg Gly Thr Asp Glu Cys
            875                 880                 885

GCG ATC GAA AGC ATA GCG CTG GCG GCC ACC CCG ATT CCT AAG TTG        1389
Ala Ile Glu Ser Ile Ala Leu Ala Ala Thr Pro Ile Pro Lys Leu
            890                 895                 900

TAG                                                                1392
``` hereinafter referred to as SEQ ID NO:3;

```
GACACGCCUG CCAACUGCAC CUACCCCGAC CUGCUGGGCA CCUGGGUCUU CCAGGUGGGC    60

UCCAGCGGCU CCCAGCGCGA UGUCAACUGC UCGGUGAUGG GACCCCCAGA AAAAAAAGUG   120

GUGGUGCACC UCAAGAAGUU GGAUACAGCA UAUGAUGACU UGGCAAUUC CGGCCAUUUC   180

ACCAUCAUUU ACAAUCAAGG CUUUGAGAUU GUGUUGAAUG ACUACAAGUG GUUCGCCUUU   240

UUUAAGUAUA AAGAAGAGGG UGGCAAGGUA ACCAGUUACU GCCACGAGAC CAUGACUGGC   300

UGGGUCCAUG ACGUGCUGGG CCGGAACUGG GCCUGUUUCA CUGGAAGGAA GACAGGAAAU   360

ACCUCGGAGA ACGUGAACGU GAACACAGCA CGCCUUGCGG GUCUCGAGGA AACGUAUUCU   420

AAUAGGCUCU ACAGAUAUAA CCAUGACUUU GUGAAAGCUA UCAAUGCCAU UCAGAAGUCU   480

UGGACUGCAG CCCCAUACAU GGAAUAUGAG ACUCUUACCC UAAAAGAGAU GAUUAGGAGA   540

GGUGGUGGCC AUAGCCGGAG AAUUCCAAGG CCCAAACCUG CACCAAUCAC UGCUGAAAUA   600

CAGAAAAAGA UUUUGCAUUU GCCAACAUCC UGGGAUUGGA GAAACGUUCA UGGUAUCAAU   660

UUUGUUACUC CUGUUCGAAA CCAAGGGUCU UGUGGAAGCU GCUACUCAUU UGCUUCUAUG   720

GGGAUGAUGG AAGCAAGAAU CCGCAUACUA ACCAACAACA CUCAGACCCC GAUCUUGAGU   780
```

-continued

```
CCUCAGGAGG UUGUGUCUUG CAGUCAGUAU GCUCAAGGCU GUGAAGGUGG CUUCCCUUAC  840

CUCAUCGCAG GGAAGUAUGC CCAGGACUUU GGGUUGGUGG AAGAGGACUG UUUCCCCUAC  900

ACAGGCACGG AUUCGCCGUG CAGACUGAAA GAGGGCUGCU UCCGGUACUA UUCCUCCGAG  960

UACCACUACG UGGGCGGUUU CUACGGGGGC UGCAAUGAAG CCCUGAUGAA GCUUGAGCUG 1020

GUCCAUCAGG GGCCCAUGGC CGUCGCCUUU GAAGUCUACG ACGACUUCCU CCACUACCGC 1080

AAGGGCGUCU ACCACCACAC GGGGCUGCGA GACCCUUUCA ACCCCUUCGA GCUGACCAAU 1140

CAUGCUGUGC UGCUGGUGGG CUAUGGCACU GACGCGGCCU CUGGACUGGA UUACUGGAUU 1200

GUUAAAAACA GCUGGGGCAC CAGCUGGGGU GAGAACGGUU ACUUCCGCAU CCGCAGAGGA 1260

ACCGACGAGU GUGCGAUCGA AAGCAUAGCG CUGGCGGCCA CCCCGAUUCC UAAGUUG    1317
``` hereinafter referred to as SEQ ID NO:5;

```
AUGGGUCCCU GGUCCGGCUC GCGGCUCGUC GCUCUCUUGC UGCUCGUCUA UGGCGCUGGC   60

UCCGUGCGCG GGGACACGCC UGCCAACUGC ACCUACCCCG ACCUGCUGGG CACCUGGGUC  120

UUCCAGGUGG GCUCCAGCGG CUCCCAGCGC GAUGUCAACU GCUCGGUGAU GGGACCCCCA  180

GAAAAAAAAG UGGUGGUGCA CCUCAAGAAG UUGGAUACAG CAUAUGAUGA CUUUGGCAAU  240

UCCGGCCAUU UCACCAUCAU UUACAAUCAA GGCUUUGAGA UUGUGUUGAA UGACUACAAG  300

UGGUUCGCCU UUUUUAAGUA UAAAGAAGAG GGUGGCAAGG UAACCAGUUA CUGCCACGAG  360

ACCAUGACUG GCUGGGUCCA UGACGUGCUG GGCCGGAACU GGGCCUGUUU CACUGGAAGG  420

AAGACAGGAA AUACCUCGGA GAACGUGAAC GUGAACACAG CACGCCUUGC GGGUCUCGAG  480

GAAACGUAUU CUAAUAGGCU CUACAGAUAU AACCAUGACU UUGUGAAAGC UAUCAAUGCC  540

AUUCAGAAGU CUUGGACUGC AGCCCCAUAC AUGGAAUAUG AGACUCUUAC CCUAAAAGAG  600

AUGAUUAGGA GAGGUGGUGG CCAUAGCCGG AGAAUUCCAA GGCCCAAACC UGCACCAAUC  660

ACUGCUGAAA UACAGAAAAA GAUUUUGCAU UUGCCAACAU CCUGGGAUUG GAGAAACGUU  720

CAUGGUAUCA AUUUUGUUAC UCCUGUUCGA AACCAAGGGU CUUGUGGAAU CUGCUACUCA  780

UUUGCUUCUA UGGGGAUGAU GGAAGCAAGA AUCCGCAUAC UAACCAACAA CACUCAGACC  840

CCGAUCUUGA GUCCUCAGGA GGUUGUGUCU UGCAGUCAGU AUGCUCAAGG CUGUGAAGGU  900

GGCUUCCCUU ACCUCAUCGC AGGGAAGUAU GCCCAGGACU UUGGGUUGGU GGAAGAGGAC  960

UGUUUCCCCU ACACAGGCAC GGAUUCGCCG UGCAGACUGA AAGAGGGCUG CUUCCGGUAC 1020

UAUUCCUCCG AGUACCACUA CGUGGGCGGU UUCUACGGGG CUGCAAUGA AGCCCUGAUG 1080

AAGCUUGAGC UGGUCCAUCA GGGGCCCAUG GCCGUCGCCU UUGAAGUCUA CGACGACUUC 1140

CUCCACUACC GCAAGGGCGU CUACCACCAC ACGGGGCUGC GAGACCCUUU CAACCCCUUC 1200

GAGCUGACCA AUCAUGCUGU GCUGCUGGUG GGCUAUGGCA CUGACGCGGC CUCUGGACUG 1260

GAUUACUGGA UUGUUAAAAA CAGCUGGGGC ACCAGCUGGG GUGAGAACGG UUACUUCCGC 1320

AUCCGCAGAG GAACCGACGA GUGUGCGAUC GAAAGCAUAG CGCUGGCGGC CACCCCGAUU 1380

CCUAAGUUGA AG                                                    1392
``` hereinafter referred to as SEQ ID NO:6;
the complement of SEQ ID NO:1, SEQ ID NO:3, SEQ ID NO:5, or SEQ ID NO:6, or a fragment of at least eighteen consecutive nucleotides thereof, which will selectively hybridize to a protein having dipeptidylaminopeptidase activity.

This invention also encompasses recombinant vectors comprising one of the above-described nucleic acids as well as host cells harboring said recombinant vectors.

The bovine dipeptidylaminopeptidase 1 (bDAP 1) protein has a sequence as depicted in SEQ ID NO:2, which is naturally encoded by the nucleotide sequence of SEQ ID NO:1.

As is common with proteins which are post-translationally processed through the Golgi, endoplasmic reticulum, stored in internal vacuoles or are externally translocated, the cDNA of bDAP 1 demonstrates the presence of a signal peptide. The full length cDNA sequence for the pre-bDAP 1 protein is as depicted in SEQ ID NO:3.

The first 72 residues of Sequence ID No. 3 encode a 24 amino acid signal peptide sequence resulting in a pre-bDAP 1 molecule having an amino acid sequence as shown in SEQ ID NO:4.

DETAILED DESCRIPTION AND PREFERRED EMBODIMENTS

The terms and abbreviations used in this document have their normal meanings unless otherwise designated. For example "_C" refers to degrees Celsius; "N" refers to normal or normality; "mmol" refers to millimole or millimoles; "g" refers to gram or grams; "ml" means milliliter or milliliters; "M" refers to molar or molarity; "µg" refers to microgram or micrograms; and "µl" refers to microliter or microliters.

The amino acids abbreviations are as set forth in 37 C.F.R. § 1.822 (b)(2) (1994). One skilled in the art would recognize that certain amino acids are prone to rearrangement. For example, Asp may rearrange to aspartimide and isoasparigine as described in I. Schön, et al., *International Journal of Peptide and Protein Research*, 14:485–94 (1979) and references cited therein. These rearrangement derivatives are included within the scope of the present invention. Unless otherwise indicated, the amino acids are in the L configuration.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides uridine, cytidine, guanosine, and adenosine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. To insure against improper translation, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other bovine dipeptidylaminopeptidase 1 variants. This term may also be employed in the sense that such antibodies may be used to differentiate between the human bovine dipeptidylaminopeptidase 1 protein and analogous proteins derived from other species.

The term "PCR" as used herein refers to the widely-known polymerase chain reaction employing a thermally-stable polymerase.

"Precursor polypeptide" refers to a polypeptide or protein which comprises an even number of amino acids extended from the amino terminus of the desired polypeptide of interest.

"Processed polypeptide" refers to a polypeptide or protein wherein the N-terminal dipeptide or dipeptides have been removed to yield the desired polypeptide of interest.

"Support surface" refers to any solid or semi-solid surface or matrix that can be used as is or easily derivatized or activated to bond a protein, exhibits minimal non-specific adsorption, is physically mechanically and chemically stable, is highly porous to provide ligand accessibility, and can be regenerated without deteriorating the surface.

"MR-KPB-hPI" as used herein as Met-Arg-Human Proinsulin having Lys at position 28 and Pro at position 29 of the corresponding insulin B-chain. This human insulin analog precursor protein may also be expressed in the following nomenclature style; Met-Arg-Human Proinsulin Analog (B28 Lys, B29 Pro).

"KPB-hPI" refers to Human Proinsulin having Lys at position 28 and Pro at position 29 of the corresponding insulin B-chain. This human insulin analog processed protein may also be expressed in the following nomenclature style; Human Proinsulin Analog (B28 Lys, B29 Pro).

"GFpNA" refers to Gly-Phe p-nitroanilide.

"RRBNA" refers to Arg-Arg-$\beta$-naphthylamide.

"Z-RRBNA" refers to benzyloxycarbonyl-RRBNA.

The present invention is particularly useful for efficiently converting precursor polypeptides or proteins into processed polypeptides or proteins. For instance, if human growth hormone is the desired polypeptide, one merely expresses a precursor of human growth hormone (in one case, a Met-Asp-human growth hormone), then subjects this precursor to bDAP 1 activity to release the dipeptide Met-Asp and the desired processed polypeptide, human growth hormone. The processed peptide is not required to be the "natural" wild-type polypeptide, as often it is desirable to produce analogs or intermediates. Other precursor polypeptides which may be processed using the present invention include Met-Arg-human growth hormone, Met-Arg-Human Proinsulin, Met-Tyr-Human Proinsulin, Met-Arg-Human Proinsulin Analog (B28 Lys, B29 Pro), Met-Tyr-Human Proinsulin Analog (B28 Lys, B29 Pro), Met-Arg-Human Proinsulin Analog (B10 Asp, des B28-30), Met-Tyr-Human Proinsulin Analog (B10 Asp, des B28-30), and Met-Tyr-Human Proinsulin Analog (des 64). Insulin Analog (B28 Lys, B29 Pro) is disclosed in European Patent Application Serial No. 90301224.3 while Insulin Analog (B10 Asp, des B28-30) is disclosed in European Patent Application Serial No. 92305678.2.

Processing of Met-Arg-Human Proinsulin and Met-Arg-Human Proinsulin Analogs with bovine DAP 1 is disclosed in Becker et al., U.S. Pat. No. 5,126,249, issued Jun. 30, 1992, the entire teaching of which is herein incorporated by reference. In addition, bDAP 1 may be used to sequentially remove more than one set of dipeptides from the amino-terminus of precursor polypeptides.

It will be readily apparent to one of skill in the art that alternate signal peptides may be used in place of the native signal peptide of the protein and that although it is preferred to use the native signal sequence when expressing the pre-bDAP 1 protein recombinantly in a mammalian cell environment, other signal peptides (e.g., the alpha mating factor signal peptide in yeast) may be more desirable when expressing the pre-bDAP 1 protein in other eukaryotic or prokaryotic systems. It is well known in the art that signal peptides facilitate the extracellular discharge of secretory proteins in both prokaryotic and eukaryotic environments. It has been shown that the addition of a heterologous signal peptide to a normally cytosolic protein may result in the extracellular transport of the normally cytosolic protein in *E. coli*. MacIntyre, et al., (1987) *Journal of Biological Chemistry*, 262:8416–8422. It is well known in the art that alternate signal peptide sequences may function with heterologous coding sequences. For instance, a DNA sequence encoding the signal peptide from a receptor such as the secretin receptor may be substituted for the DNA sequence encoding the signal peptide of the PROTEIN resulting in a heterologous protein retaining PROTEIN characteristics.

Signal peptides are well known in the art which could be similarly incorporated into the pre-bDAP 1 structure to facilitate extracellular translocation or intracellular destination. The recombinant production of such proteins maybe accomplished by the addition of a DNA sequence encoding a signal peptide appropriate to the host organism inserted 5' to, and in reading frame with, the bDAP 1 protein coding sequence. The signal peptide may be microbial or mammalian, but is preferably is mammalian. In the preferred practice of the invention the signal peptide used is a signal peptide native to a secretory protein of the host cell line. In the most preferred practice of the invention as exemplified herein, the signal peptide is the native 24 amino acid bDAP 1 presequence.

Furthermore, the signal sequence may be wholly synthetic. Synthetic "idealized" signal peptides have been shown to function in both prokaryotic and eukaryotic environments. von Heijne, G. (1990) J. Membrane Biol. 115: 195–201. The principles of signal peptides are similar in both prokaryotic and eukaryotic organisms. Both prokaryotic and eukaryotic signal peptides possess an overall three domain (region instead of domain which has a specific technical meaning for protein structure) structure and with no precise sequence conservation necessary to preserve function. von Heijne, G., supra. Generally, the presence of basic and/or charged amino acid residues near the amino terminus of the structural protein inhibits secretion. Yamane, K., et al. (1988) *Journal of Biological Chemistry*, 263:19690–19696, Summers, R. G., et al. (1989) *Journal of Biological Chemistry*, 264:20082–20088. In order to insure the efficient cleavage of the signal peptide from the fusion protein construct, it is desirable to maintain the nature of the amino acid sequence at the interface between the signal peptide and the coding sequence of the mature art protein. Conservation of charge and hydrophobicity and the elimination of charged residues immediately downstream of the signal peptide cleavage point are generally important to efficient translocation. However, it is not critical that any one particular amino acid sequence be maintained.

The pre-bDAP 1 protein is processed to yield the three subunits of the functional bDAP 1 protease. The three subunits are:

(1) the 206 amino acid (a) subunit encoded by nucleotides? 1 through 618 of SEQ ID NO:1;

(2) the 164 amino acid (b) subunit encoded by nucleotides 619 through 1110 of SEQ ID NO:1; and (3) the 69 amino acid (g) subunit encoded by nucleotides 1111 through 1317 of SEQ ID NO:1.

One will note that the amino acid sequence of the junction between the (a) and (b) (between beta and gamma) subunits as illustrated in SEQ ID NO:1 provided by cDNA information is His-His-Thr-Gly-Leu-Arg. However the C-terminus of the mature (a) (beta) subunit ends in the sequence His-His-Thr-Gly. It is believed that the Leu-Arg residues are removed during post-translational processing of the (a) (beta) subunit following the cleavage of the (a) and (b) subunits (beta and gamma) at the Arg-Asp junction. Consequently, the mature form of the (a) subunit (beta) as found in the mature trimeric protein and as indicated in does not include these two C-terminal residues.

The availability of the entire translated amino acid sequence for bDAP 1 allows us to draw some reasonable interpretations about the functional description of the enzyme. The whole polypeptide shows homology to rat DAP 1. The a subunit does not show any sequence homology to other proteins in the papain family. The b and g subunits show extreme homology to the papain family. When the active sites and the substrate binding pockets are compared, even greater homologies are observed: the active sites proposed in papain are also present in bovine DAP 1 and the substrate binding pocket proposed in papain is also conserved. The hydrophobicity of the pocket in papain leads to the preference of hydrophobic residue at P2 position. In cathepsin B, the S205 residue in the bottom of the binding pocket is replaced by glutamic acid residue. The replacement has been used to explain the observation that cathepsin B can use both hydrophobic and basic residues at the P2 position. The conservation of both active site and substrate binding pocket led us to propose that the DAP 1 b-g portion may actually function as an endopeptidase. The function of the a subunit may be to modulate the endopeptidase activity to be a dipeptidylaminopeptidase. Assuming that the b-g portion can fold in a similar 3-D structure as it does in papain, a two domain structure with L domain (mainly beta subunit) and R domain (part of beta subunit and all of gamma subunit) separated by a substrate binding cleft, we can image that the additional a subunit may be in a position to block one side of the substrate binding cleft thus only dipeptides can be present in the cleft, altering the endopeptidase activity of b-g to a dipeptidylaminopeptidase.

The DNA sequences of the present invention may be used for the recombinant production of bDAP 1. For example, the DNA sequence encoding pre-bDAP 1 may be incorporated into a vector for eukaryotic expression and intracellular processing enzymes native to mammalian expression systems will result in the production and secretion of mature bDAP 1 into the culture media.

For prokaryotic expression, the pre-bDAP 1 molecule once isolated from the microbial expression host will be processed in vitro to lead to the mature protein. Alternatively, the individual DNA sequences encoding the individual (a), (b) and (g) subunits may be separately expressed and renatured into the mature functional bDAP 1 protein in vitro.

The bDAP 1 may also be produced by recombinant methods. Construction of suitable vectors containing the desired coding and control sequences employ standard ligation techniques. Isolated plasmids or DNA fragments are cleaved, tailored, and religated in the form desired to form the plasmids required.

To effect the translation of the bDAP 1 coding sequence, one inserts the bDAP 1 coding sequence in any of a plethora of appropriate recombinant DNA expression vectors through the use of appropriate restriction endonucleases. The bDAP 1 coding sequence is designed and modified to possess restriction endonuclease cleavage sites at either end of the transcript to facilitate isolation from and integration into these expression and amplification and expression plasmids. The coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the bDAP 1 coding sequence with control sequences to achieve proper in-frame reading and expression of the bDAP 1 protein.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene*, 2:95 [1977]), pBR322 contains genes for ampicillin and tetracycline resistance and, thus, provides easy means for identifying transformed cells. The pBR322 plasmid, or other microbial plasmid must also contain or be modified to contain promoters and other control elements commonly used in recombinant DNA construction.

The bDAP 1 coding sequence is positioned so as to be operably associated with the promoter and ribosome binding site of the expression vector, both of which are functional in the host cell in which the bDAP 1 is to be expressed. In the preferred practice of the invention, the promoter-operator region is placed in the same sequential orientation with respect to the ATG start codon of DNA sequence encoding the bDAP 1 as the promoter-operator occupies with respect to the ATG-start codon of the gene from which it was derived. Synthetic or modified promoter-operator regions such as the tac promoter are well known in the art. When employing such synthetic or modified promoter-operator regions they should be oriented with respect to the ATG start codon of the bDAP 1 coding sequence as directed by their creators.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See. e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% metacresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology*, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
| --- | --- |
| DH5α | F− (φ80dlacZΔM15), Δ(lacZYA-argF)U169 supE44, λ−, hsdR17($r_K^-$, $m_K^+$), recA1, endA1, gyrA96, thi-1, relA1 |
| HB101 | supE44, hsdS20($r_B^-$ $m_B^-$), recA13, ara-14, proA$_2$, lacY1, galK2, rpsL20, xyl-5, mtl-1, mcrB, mrr |
| JM109 | recA1, e14−(mcrA), supE44, endA1, hsdR17($r_K^-$, $m_K^+$), gyrA96, relA1, thi-1, Æ(lac-proAB), F'[traD36, proAB+ lacI$^q$,lacZ ÆM15] |
| RR1 | supE44, hsdS20($r_B^-$ $m_B^-$), ara-14 proA$_2$, lacY1, galK2, rpsL20, xyl-5, mtl-5 |
| χ1776 | F−, ton, A53, dapD8, minA1, supE42 (glnV42), Δ(gal-uvrB)40, minB2, rfb-2, gyrA$_2$5, thyA142, oms-2, metC65, oms-1, Δ(bioH-asd)29, cycB2, cycA1, hsdR2, λ− |
| 294 | endA, thi−, hsr−, hsm$_K^+$ (U.S. Pat. No. 4,366,246) |
| LE392 | F−, hsdR514 (r−m−), supE44, supF58, lacY1, or Δlac(I-Y)6, galK2, glaT22, metB1, trpR55, λ− |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ATCC 31608, and is described in U.S. Pat. No. 4,551,433, issued Nov. 5, 1985.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., Nature (London), 275:615 (1978); and Goeddel et al., Nature (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. dipeptidylaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human bovine dipeptidylaminopeptidase 1-encoding nucleic acids of the present invention. Exemplary host cells suitable for use in the present invention are listed in Table I

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |

TABLE I-continued

| Host Cell | Origin | Source |
|---|---|---|
| H4IIEC3 | Rat Hepatoma | ATCC CCL 1600 |
| C1271 | Mouse Fibroblast | ATCC CCL 1616 |
| 293 | Human Embyronal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, Cell, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., Proceedings of the National Academy of Sciences (USA), 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovarus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., *Nature* (London), 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et aL, European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |

TABLE II-continued

| Original Residue | Exemplary Substitutions |
| --- | --- |
| Gly | Pro, Ala |
| His | Asn, Gln |
| Ile Leu, Val | |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein of the present invention may also be induced by alterations of the nucleic acid compounds which encodes these proteins. These mutations of the nucleic acid compounds may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode the proteins of the present invention. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human bovine dipeptidylaminopeptidase 1 molecule may be produced using synthetic methodology. This synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See, e.g., M. J. Gait, ed., OLIGONUCLEOTIDE SYNTHESIS, A PRACTICAL APPROACH, (1984).

The synthetic human bovine dipeptidylaminopeptidase 1 gene may be designed to possess restriction endonuclease cleavage sites at either end of the transcript to facilitate isolation from and integration into expression and amplification plasmids. The restriction sites are chosen so as to properly orient the coding sequence of the target enzyme with control sequences to achieve proper in-frame reading and expression of the bovine dipeptidylaminopeptidase 1 molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference. In addition to the deoxyribonucleic acid compounds described supra the present invention also encompasses the ribonucleic acid compounds of SEQ ID NO:5, SEQ ID NO:6, the complementary ribonucleic acid, or a fragment of either SEQ ID NO:5 or SEQ ID NO:6, or the complement thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1, SEQ ID NO:3, SEQ ID NO:5, or SEQ ID NO:6.

The present invention also provides probes and primers useful for molecular biology techniques. A compound which is SEQ ID NO:1, SEQ ID NO:3, SEQ ID NO:5, or SEQ ID NO:6, or a complementary sequence of one of these sequences, or a fragment thereof, and which is at least 18 base pairs in length, and which will selectively hybridize to genomic DNA or messenger RNA encoding a bovine dipeptidylaminopeptidase 1, is provided. Preferably, the 18 or more base pair compound is DNA.

The term "selectively hybridize" as used herein may refer to either of two situations. In the first such embodiment of this invention, the nucleic acid compounds described supra hybridize DNA or RNA encoding a human bovine dipeptidylaminopeptidase 1 under more stringent hybridization conditions than these same nucleic acid compounds would hybridize to an analogous bovine dipeptidylaminopeptidase 1 of another species, e.g. murine or primate. In the second such embodiment of this invention, these probes hybridize to DNA or RNA encoding a bovine dipeptidylaminopeptidase 1 of the present invention under more stringent hybridization conditions than other related compounds, including nucleic acid sequences encoding other human bovine dipeptidylaminopeptidase 1 enzymes.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprise one of the isolated DNA sequences of SEQ ID NO: 1 and SEQ ID NO:3.

Yet another embodiment of the invention is a method of using a bovine dipeptidylaminopeptidase 1-encoding gene to transform a cell. There is a wide variety of transformation techniques applicable to both prokaryotic and eukaryotic cells which will not be discussed, because such methods are old in the art.

A further embodiment of the invention consists of a method of using a host cell to express bovine dipeptidylaminopeptidase 1. In this embodiment, a host cell, either prokaryotic or eukaryotic, that has been transformed is cultured in an appropriate medium until a substantial cell mass has been obtained. Fermentation of transformed prokaryotes and mass cell culture of transformed eukaryotic cells is well known in the art and will not be discussed for that reason.

The second step of this embodiment is the isolation of bovine dipeptidylaminopeptidase 1 from the cultured cells. Processes for isolating this protein are discussed infra.

EXAMPLE 1

Isolation of Bovine Spleen Total mRNA

Bovine spleen Total RNA was isolated from 2 g of tissue frozed at −70° C. using acid phenol method [Bradley, et al., *Biotechniques*, 6:114 (1988)]. mRNA was isolated from the total RNA using the PolyA tract kit from Premaga Madison, Wis., USA) or by oligodT cellulose column using a kit purchased from Bethesda Research Laboratories (BRL, Bestheda, Md. USA). For first strand cDNA synthesis, about 100 ng of mRNA was used using first strand cDNA synthesis kit purchased from Strategene according to the manufacturers instructions. The oligo dT primer provided in the kit or specific primers were used to direct the cDNA synthesis. Once finished, the 50 $\mu$l final volume was adjusted to 100 $\mu$l using water and stored at −20° C.

PCR primers based on the internal fragments and the N-terminal fragments have been designed and used in PCR reactions. Once a fragment is amplified, cloned and sequenced, new primers are also designed based on the exact cDNA sequencing. For cloning both 5' and 3' ends, adapter and oligo dT-adapter primers were synthesized. PCR was performed using a commercially available machine in substantial accordance with the instructions provided by the manufacturer except 150 $\mu$M 7-deaza-dGTP was also presented besides 200 $\mu$M each of dATP, dCTP, dTTP, and 50 $\mu$M dGTP. The application of 7-deaza-dGTP has been shown to eliminate some of the nonspecific background while it has no effect on the Taq DNA polymerase itself. Generally 32–35 cycles were used at 94° C. 1 min, 50–60° C. 1 min and 72° C. 2 min with final extention 7 min at 72° C.

EXAMPLE 2

Cloning of PCR Fragments

To clone PCR products, three methods were used during these studies. The first one using the Klenow fragment of DNA polymerase I to blunt-end the PCR fragments and the fragments were cloned into PBLUESCRIPT KSII(−)™ vector (commercially available from Stratagene, Inc, La Jolla, Calif. 92037) which had been digested with the EcoRV restriction endonuclease and plated on L-broth plates supplemented with 50 $\mu$g/ml ampicillin and 100 $\mu$g/ml X-Gal. White colonies were selected and analyzed for inserts.

The second method utilized a commercially available, linearized vector, pCR1000 (Invitrogen, Calif., USA), which is specifically designed to clone the PCR products.

The third method was "forced cloning" which utilized the known restriction enzymes. The PCR products were treated with proteinase K before restriction and cloning. J. S. Crowe, et al., *Nucleic Acids Research*, 19:184 (1991). Consensus DNA coding sequence was derived from at least two independent clones.

To clone 3' end including untranslated region, a modified version of the RACE procedure as described in Frohman, et al., *Proceedings of the National Academy of Sciences (USA)*, 85:8998 (1988), was employed. The first strand cDNA was synthesized similar to the regular first strand cDNA synthesis method except Adapter-dT primer was used rather than the oligodT primer employed therein. In the PCR reaction, 1 $\mu$l of the cDNA was used to be amplifed by primers Adaptor and Int-1 at 60° C. annealing temperature.

The RACE procedure was further modified to amplify the 5' end of the cDNA in the following manner. The first strand cDNA was synthesized using INT-2 primer. The subsequent procedure was performed in substantial accordance with the teaching of Jain, et al., *Biotechniques*, 12:58 (1992). After the first strand cDNA synthesis was done, it was heat inactivated at 95° C. for 10 min. The mixture was treated with 0.4 U RNaseH at 37° C. for 30 minutes before it was heat inactivated at same condition. Then the whole mixture was adjusted to 400 $\mu$l final volume in water and ultrafiltered by passing through 30 kD Milipore ultrafiltration units. The DNA was recovered in a centrifuge tube and dried under vaccum.

The first strand cDNA was tailed with dATP by using a commercially available protocol according to the manufacturer's directions, except that 125 $\mu$M dATP was used. The terminal transferase was heat inactivated and the volume was adjusted to 100 $\mu$l using water. Ten microliters of the tailed cDNA is used in a three round PCR using primers oligodT-adaptor and internal primer AB-2 at 94° C. 1 minute, 48° C., 1 minute, 72° C. 2 minutes. The reaction mixture was once more filtered through an ultrafiltration unit and all of the recovered DNA was used in the second round PCR for 32 cycles at 94° C. 1 minute, 56° C. 1 minute, 72° C. 2 minutes using primers DAI13 and adapter.

DNA Sequencing:

Sequence determinations are performed with dideoxy chain termination with an automated flourescent dye DNA sequencer (Applied Biosystems) or manually using [$\alpha$-$^{35}$S] dATP followed by autoradiography. For manual sequencing either a T7 primer or a M13F (forward) primer is used.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The desired plasmid may be isolated from *E. coli* containing these plasmids using standard procedures such as cesium chloride DNA isolation or isolation in a QIAGEN™ column.

Any plasmid comprising the gene of the present invention is readily modified to construct expression vectors that produce bovine dipeptidylaminopeptidase 1 in a variety of organisms, including, for example, *E. coli*, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, CURRENT PROTOCOLS IN MOLECULAR BIOLOGY, 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2 or SEQ ID NO:4, said method comprising transforming a host cell with a recombinant DNA vector that comprises an isolated DNA sequence which encodes SEQ ID NO:2 or SEQ ID NO:4. The preferred host cell is AV12.

The preferred vector for expression is one which comprises SEQ ID NO:1 or SEQ ID NO:3. Another preferred host cell for this method is *E. coli*. An especially preferred expression vector in *E. coli* is one which comprises SEQ ID NO:1 or SEQ ID NO:3. Transformed host cells may be cultured under conditions well known to skilled artisans such that SEQ ID NO:2 or SEQ ID NO:4 is expressed, thereby producing the bovine dipeptidylaminopeptidase 1 in the recombinant host cell.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', $Fab_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g., C. Milstein, HANDBOOK OF EXPERIMENTAL IMMUNOLOGY, (Blackwell Scientific Pub., 1986); J. Goding, MONOCLONAL ANTIBODIES: PRINCIPLES AND PRACTICE, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No.

4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., *Science* 242:423–426 (1988); PCT Publication No. WO 88/01649, which was published Mar. 10, 1988; U.S. Pat. No. 5,260,203, issued Nov. 9, 1993, the entire contents of which are herein incorporated by reference. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in an ex vivo analysis of the presence of bovine dipeptidylaminopeptidase 1. Such assays are well known to those skilled in the art. In addition, such antibodies may be used in the preparation of immunosorbent chromatographic columns. The preparation and use of such columns are well known to those skilled in the art.

An especially preferred method of using the proteins of the present invention concerns immobilizing the peptidase on a suitable support surface or matrix. The ordinarily skilled artisan will readily understand and appreciate the many commercially-available solid support surfaces and matrices. By way of illustration not meant to limit the scope of the invention, solid support surfaces may include inorganic materials such as porous silica, controlled pore glass, and hydroxyapatite. Synthetic organic polymers such as polyacrylamide, polymethacrylate, and polystyrene are also illustrative support surfaces. In addition, polysaccharides such as cellulose, dextran, SEPHADEX®, SEPHAROSE®, and agarose are further illustrative examples of support surfaces consistent with the invention. Other support surfaces such as membranes and fibers are also consistent with the claimed process. An example of a commercially available membrane is the ACTI-MOD® quaternary amine module (FMC BioProducts).

Preferred support surfaces are those which do not adversely affect bDAP 1 once bound to the surface. Commercially-available polysaccharide matrices formed into various sized beads are more preferred because they are porous, easy to handle, and are well known and understood in the biochemical purification art. More highly preferred support surfaces are commercially-available anion exchange resins. The most preferred support surface is Q SEPHAROSE® resin (Pharmacia). See *Affinity Chromatography Principles & Methods*, Pharmacia Fine Chemicals, (1983); *Biotechnology Products Catalog* 1993, Pharmacia Biotech Inc, 800 Centennial Ave., Piscataway, N.J. 08854.

A wide assortment of schemes for immobilizing or coupling proteins to support surfaces has developed over the past few decades. Both covalent and non-covalent immobilization of bDAP 1 to the support surface is consistent with the invention as are bridges that serve to link the support surface to the bDAP 1 enzyme.

Enzyme immobilization is most usually accomplished using solid supports, generally chromatography resins, that have been modified or activated to include functional groups that permit the covalent coupling of resin to enzyme. Typically aliphatic linker arms are employed. An example of a commercially available covalent immobilization resin is Activated CH SEPHAROSE® 4B (Pharmacia). It is one of many types of chemistries that Pharmacia has attached to the SEPHAROSE® 4B base matrix. In general, activated resins cost significantly more than anion exchange resins of the same base matrix, are not available in as wide of a variety of base matrix types as ion exchange chromatographic media and may therefore be more limited in their ability to handle low clarity column charges or high mobile phase flow rates.

Cyanogen bromide and carbodiimide coupling of proteins to polysaccharide based beads such as SEPHAROSE® (Pharmacia) are also illustrative of direct coupling schemes consistent with the invention. Direct couplings generally do not orient the bound proteins in any particular fashion; however, some types of direct couplings are able to reproducibly orient the bound protein onto the support surface.

The bDAP 1 enzyme may also be noncovalently attached to a solid support surface, through, for example, ionic or hydrophobic mechanisms. A large variety of ion exchange and hydrophobic interaction chromatography resins are available from a large number of commercial sources, at lower cost than the activated, covalent immobilization resins.

A potential drawback to noncovalent immobilization is that the enzyme binding is usually reversible. Moderate levels of salts, solvents, pH change or even other proteins can lead to partial or complete desorption of the enzyme from the resin. In most instances, it would be difficult to identify conditions in which enzyme binding to noncovalent resins is tight, in which the enzyme maintains a high degree of functional activity and stability, and in which the enzyme reactants do not themselves bind to the resin.

Most unexpectedly, a key element in the presently disclosed invention was the highly opposed affinities of bDAP 1 and MR-KPB-hPI for an anion exchange resin at the acidic pH at which bDAP 1 is maximally active. Based on chromatographic behavior and isoelectric focusing, bDAP 1 is believed to have an abundance of negative charges at acidic pH. Consequently, it is believed that bDAP 1 binds strongly to the cationic functional groups of anion exchange resins, while MR-KPB-hPI or proinsulin do not bind even when they are present in large stoichiometric excess.

However, the reversibility of noncovalent enzyme binding also represents an advantage over covalent immobilization. Generally, noncovalent resin binding can be easily and repeatedly reversed. If a column resin requires regeneration because of loss of performance or increases in back pressure, the enzyme may be mildly desorbed from the resin prior to exposure of the resin to the harsh conditions of regeneration—conditions which would most likely destroy the enzyme if it remained attached to the resin. Once the resin is regenerated, it can be used to capture a new or repurified batch of enzyme.

Other immobilizing schemes may orient bDAP 1 such that its catalytic site remains exposed. One such scheme utilizes the natural carbohydrate found on the enzyme. By first oxidizing the carbohydrate moieties to the corresponding aldehydes, then reacting the aldehyde with a primary amino group on the support surface, it is possible to link bDAP 1 in an advantageous orientation.

Many types of bridges that connect bDAP 1 to the support surface are possible and include small organic linkers which covalently bind bDAP 1 to the support surface. These so called spacer arms are acceptable and preferably do not interact with proteins once the bridge has been formed.

Larger multivalent molecules bound to the support surface which are capable of binding several bDAP 1 molecules describe another type of bridge. Specific immunoadsorbants bound to the support surface that non-covalently bind bDAP 1 represent yet another type of bridge. Epitope specific, anti-bDAP 1, monoclonal antibodies are one example of a specific immunoadsorbant that is capable of orienting bDAP 1 onto the support surface. By preparing high affinity monoclonal antibodies to a bDAP 1 epitope distant from the catalytic site, then chemically bonding the antibody to the support surface and allowing bDAP 1 to bind to the antibodies, it is possible to orient bDAP 1 in a favorable configuration on the support surface.

The above discussion is in no way meant to limit the scope of the invention. The ordinarily skilled artisan will know numerous other schemes for linking proteins to support surfaces. Moreover, the choice of support surface and the method of immobilizing bDAP 1 is largely a matter of convenience and depends on the practitioner's familiarity with, and preference for, various supports surfaces, as well as his preference for various immobilizing schemes, and knowledge of the substrate. Finally, the quantity of available bDAP 1 and the overall purpose and setting in which precursor proteins are converted to processed proteins will influence the choice of support surface and immobilization method.

Once the bDAP 1 has been immobilized onto a support surface, conversion of precursor polypeptides into processed polypeptides can be accomplished under a variety of suitable conditions. The preferred way is to pack a chromatography column with immobilized bDAP 1 so that the substrate of interest (precursor protein) can be passed over the immobilized enzyme surface, allowing the reaction to proceed. Because the enzyme remains attached to the support surface, it does not become physically part of the reactant mixture and is therefore available for subsequent reuse.

It is also consistent with the present invention to repeat the contacting step one or more times to ensure complete processing of precursor protein into processed protein. Thus, the reactant/product stream may be recycled over the same bDAP 1 bed one or more times or may be sequentially passed over separate bDAP 1 beds. The preferred method is to pass the precursor protein-containing stream over two or more separate bDAP 1 beds, and it is most preferred to pass the precursor protein-containing stream over three bDAP 1 beds prepared using Q SEPHAROSE® resin as the support surface.

The skilled artisan will understand that the performance of an immobilized bDAP 1 column should be monitored by following the conversion of the substrate of interest to product. Small decreases in the efficiency of the column may be improved by decreasing the column flow rate and thereby increasing the time allowed for the enzymatic reaction to occur. Ideally, the flow rate is as rapid as possible, so long as conversion of substrate to product achieves the desired yield and so long as column back pressure does not exceed operational levels. The performance of the column is also affected by column temperature and mobile phase pH. Therefore, it is advisable to monitor these parameters.

The enzymatic reaction that converts precursor polypeptides into processed polypeptides is generally conducted in an aqueous medium suitably buffered to obtain and maintain a pH from about 2.5 to about 5.5. Preferably the pH of the medium ranges from about 3.0 to about 4.5, and, most preferably, from about 3.0 to about 3.5. The pH optimum may vary slightly according to the substrate.

The skilled artisan will recognize that the pH optimum of any specific reaction will be determined by such factors as stability and solubility of the given precursor polypeptide and enzyme. In some cases, a solubilizing agent such as urea, sodium dodecylsulfate, guanidine, and the like, may be employed.

Any of a wide range of buffering agents can be employed, the primary requirement being their ability to maintain a pH within the desired range and their inability to desorb the enzyme from the support surface. Examples of typical buffering agents are sodium phosphate, sodium acetate, sodium citrate, glycine, and the like. Preferred buffering agents are sodium acetate, sodium phosphate and glycine.

The precursor polypeptides for use in the present invention are generally prepared via recombinant DNA technology. In their preparation, a nucleotide sequence coding for the desired precursor polypeptide is prepared using routine techniques for such synthesis. These methods generally involve preparation of oligonucleotides coding both for fragments of the desired coding sequence and for their complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a recombinant vector at a location which permits the product for which it codes to be expressed. A suitable vector contains at least a portion of an expression control sequence.

The following Examples are provided as a means of illustrating the present invention. They are not to be construed as imposing any limitations thereon.

After recombinant expression, bovine DAP 1 is isolated essentially as described numerous prior art publications. See, e.g., U.S. Pat. No. 5,126,249, issued Jun. 30, 1992, the entire contents of which are herein incorporated by reference.

EXAMPLE 3 bDAP 1 Activity Assay and Characterization

A) Cleavage of GF-pNA

After purification or storage, bDAP 1 enzymatic activity was usually monitored by following the cleavage of the chromogenic substrate GFpNA. Typically the assay was performed by diluting the enzyme at least 11 fold into 1.0 ml of 4 mM GFpNA in 0.05M acetic acid adjusted to pH 3.5. The rate of cleavage of Gly-Phe dipeptide was monitored at 37° C. by measuring the increase in absorbance at 405 nm. One unit of activity leads to a 0.90 OD change per minute under these conditions. Unit/ml estimates can be made assuming an extinction coefficient for free p-nitroanilide (pNA) of 9.9 mM-1 cm-1 at 405 nm.

The inhibition profile of bDAP 1 toward the substrate GFpNA was compared to that of bovine spleen DAP-I using iodoacetamide and potassium tetrathionate, sulfihydryl modifying agents known to inhibit the activity of bovine spleen DAP-I. Samples of bDAP 1 or bovine spleen DAP-I were incubated for 15 minutes at room temperature in final concentrations of 0, 0.5, 5.0 or 50 mM of either inhibitor at pH 7 in 100 mM Tris buffer. The incubated solutions were then diluted 21-fold with 4 mM GFpNA, pH 3.5. The rate of cleavage was monitored by measuring the increase in absorbance at 405 nm at 37° C. Bovine DAP-I's rate of cleavage of GFpNA was decreased more than 90% by the exposure to 5 mM iodoacetamide and was 95% inhibited by 5 mM potassium tetrathionate. There was no evidence of significant inhibition of bDAP 1 by any of the levels of iodoacetamide or potassium tetrathionate tested.

The pH optima for the GFpNA cleaving ability of bDAP 1 was determined by adjusting a buffer consisting of 0.5M Tris, phosphate and citrate with 10% HCl or 10% NaOH to various pHs within the range of 3 to 8. bDAP 1 enzyme was diluted 20-fold in a buffer containing 100 mM cysteamine and 10 mM NaCl. Bovine DAP-I was diluted 200-fold in the same buffer. A GFpNA substrate solution (4 mM) was prepared in 2% dimethylformamide. In a microtiter plate, 0.025 ml of the Tris/phosphate/citrate buffer of various pH's was combined with 0.1 ml of diluted enzyme and with 0.1 ml of substrate solution. The rate of increase of absorbance at 410 nm was determined on a plate-reader over a 30 minute period. Results indicated that the pH optima of bDAP 1 for the cleavage of GFpNA is between 3.5 and 4.0.

B) Cleavage of Gly-Arg-pNA (GRpNA)

Four mM GRpNA was prepared in 50 mM acetic acid, 50 mM glycine buffer, pH 5. HCl or NaOH was used to achieve a variety of pHs, from 5.1 to 2.3. To 180 ul of the above pH buffered substrate was added 5 ul bDAP 1 (49 milliunits/ml final). The rate of increase of absorbance at 410 nm was monitored (using a plate-reader) and the rate of increase was compared with the pH of the reaction solution. As with GFpNA the GRpNA substrate had a pH optimum around 3.5. The enzyme had little activity below pH 2.5 or above pH 5 using this substrate.

C) Cleavage of RRBNA

About 0.25 mM RRBNA or 0.25 mM Z-RRBNA prepared in either 100 mM acetic acid, pH 3.5, or 100 mM citrate buffer, pH 5.0. To 2 ml of substrate was added bDAP 1 or bovine DAP-I (about 15 milliunit/ml solution). Rates of cleavage (monitoring fluorescence increase at 410 nm with excitation at 340 nm) were monitored. Bovine DAP-I was unable to cleave either substrate. Surprisingly, bDAP 1 was able to effectively cleave the RRBNA substrate. bDAP 1 was unable to cleave the blocked amino group Z-RRBNA substrate, supporting the observation that bDAP 1 is a DAP enzyme. The pH optimum for cleavage of RRBNA was probed by monitoring the rate of RRBNA cleavage using a buffer system consisting of 50 mM acetic acid and 50 mM citrate. Various pHs were achieved using HCl or NaOH and 1.5 ml volumes were made 2.0 with 0.5 ml of a 1 mM stock solution of RRBNA (final concentration of about 0.25 mM). bDAP 1 was added (to about 15 mU/ml) and the rates of cleavage were determined. The pH optimum for cleavage of RRBNA was observed to be about 4.5, with significant activity seen over the entire range probed (pH 3.5 to pH 5.7). This surprising result suggests that bDAP 1 shares some properties with DAP III.

The skilled artisan will recognize that the optimum pH for cleavage of a substrate not only depends upon the enzyme but the substrate itself, that is, the constitution of the removed dipeptide as well as the indicator group itself. For example, using bDAP 1, GRpNA has a pH optimum of about 3.5 while the pH optimum for cleavage of Gly-Arg-7-amido-4-methylcoumarin is about pH 5, suggesting that the reporting group can effect the cleavage properties.

EXAMPLE 4 bDAP 1 Column Preparation

A 1.0 ml (0.5×5.0 cm) column of Q SEPHAROSE® Fast Flow resin (Pharmacia) was packed and equilibrated with 10 column volumes of dilute acetic acid (0.05M acetic acid, pH 3.5). A 1 unit per ml solution of bDAP 1 (prepared in accordance with Examples 1 and 2, 5.5 U per ml) was prepared by diluting a 0.27 ml volume of bDAP 1 into 1.22 ml of dilute acetic acid. The bDAP 1 solution was applied at a flow rate of 30 cm/hr (0.1 ml per minute) and the column was washed with at least 10 ml of additional dilute acetic acid. The column flow-through was measured for bDAP 1 activity using the GFpNA activity assay. No activity was detected in the column flow-through fraction eluting from the column. This indicated near quantitative binding of the bDAP 1 enzyme to the resin. The bDAP 1 level applied to this column corresponded to about 1 unit per $cm^3$ (or 5 units per $cm^2$).

EXAMPLE 5

Conversion of GFpNA to pNA Using Immobilized bDAP 1

To the column, prepared as described in Example 4, was applied a 1.0 ml solution of 0.4 mM GFpNA in 0.05M acetic acid, pH 3.5 at a flow rate of 60 cm/hr. The column effluent was monitored at 410 nm using an LKB monitor Model 2151 Variable Wavelength Monitor set at 1.56 AUFS with a 10 mm flow cell). As the solution proceeded down the column, it became yellow in color, and as it left the column an increase in absorbance was detected. Both observations indicated that the bDAP 1 column converted GFpNA to the chromogenic product pNA. This system of 1.0 ml injections of GFpNA on to the 1.0 ml (0.5×5.0 cm) immobilized bDAP 1 column was used periodically to monitor the continued availability of the bDAP 1 enzyme on the resin.

EXAMPLE 6

Conversion of Met-Arg-Human Proinsulin Analog (B28 Lys, B29 Pro)

The column, prepared as described in Example 4, was re-equilibrated with about 10 column volumes of dilute acetic acid. A 20 gm/l solution of recombinantly produced MR-KPB-hPI was obtained and adjusted to pH 3.3 with 10% v/v hydrochloric acid solution. A 5.0 ml portion of the MR-KPB-hPI solution was applied to the bDAP 1 column at room temperature at a flow rate of 60 cm/hr. The effluent was collected as 1.0 ml fractions and were diluted into 4.0 ml of 0.05M acetic acid containing 7M urea. The extent of conversion of MR-KPB-hPI to KPB-hPI was monitored on a reverse phase HPLC analytical system consisting of an Ultrasphere ODS column (Phenomenex) column eluted with a gradient of 25 to 30% acetonitrile in 0.1M ammonium phosphate, pH 7. A conversion of 40% was determined by HPLC analysis.

A second 5.0 ml portion of MR-KPB-hPI was applied to the bDAP 1 column at a flow rate of 60 cm/hr and a percentage conversion of 40% was determined by HPLC.

A third 50 ml portion of MR-KPB-hPI was applied at a flow rate of 60 cm/hr. The portion was continuously recycled for a total of 250 ml and a final percentage conversion of 75% was determined by HPLC for the portion.

A forth 5.0 ml portion of MR-KPB-hPI was applied at a flow rate of 12 cm/hr and a percentage conversion of 83% was determined by HPLC.

A fifth 60 ml portion of MR-KPB-hPI was applied at a flow rate of 12 cm/hr and a percentage conversion of 80% was determined by HPLC.

A sixth 148 ml portion of MR-KPB-hPI was applied at an average flow rate of 12 cm/hr and an average percentage conversion of 84% was determined by HPLC.

A total of 15 days elapsed during the course of the above described experiment. When the column was not exposed to the MR-KPB-hPI solution, it was washed and stored in dilute acetic acid at room temperature (20° C.). During the application of the final 213 ml of MR-KPB-hPI, when the flow was maintained at a constant 8 cm/hr, no significant decrease in percentage conversion of MR-KPB-hPI was detected suggesting that further additional amounts of MR-KPB-hPI could be processed over this resin with continued good yield. Occasional buildups of column back pressure were encountered during the course of this experiment; however, a temporary reversal of column flow or column frit replacements appeared to correct this problem. The bDAP 1 on the column was exposed to the equivalent of about five standard batch-mode MR-KPB-hPI conversion reactions (273 ml or about 5.5 gm of MR-KPB-hPI was reacted in this experiment). In batch mode, about 50–60 ml or about 1.0 gm, of MR-KPB-hPI would be reacted with 1 unit of bDAP 1. This observation supported the contention that bDAP 1 immobilized in this manner made a significant impact on bDAP 1 usage by the MR-KPB-hPI process.

EXAMPLE 7

Preparation of Larger Immobilized bDAP 1 Columns

Columns measuring 1.0×6.0 cm, 2.2×6.0 cm, and 30×10 cm were individually packed with Q SEPHAROSE® Big Bead resin (Pharmacia Chemical Company) and equilibrated with 5 column volumes of dilute acetic acid (0.05M acetic acid, pH 3.5). A solution of purified bDAP 1 (9.5 U per ml), prepared and isolated in accordance with Examples 1 and 2, was diluted to 4 U per ml in dilute acetic acid. The bDAP 1 solution was individually applied to each different column at a flow rate of 50 cm/hr. The bDAP 1 was applied in levels of 2.5 U per cm$^2$ (1.0×6.0 cm), 5.0 U per cm$^2$ (1.0×6.0 cm), and 10.0 U per cm$^2$ (1.0×6.0 cm, 2.2×6.0 cm, and 30×10 cm). Each column was washed with at least 3 additional column volumes of dilute acetic acid. The column flow-through for each column was measured for bDAP 1 activity using the GFpNA activity assay. No activity was detected in the column flow-through fraction eluting from the column. This indicated near quantitative binding of the bDAP 1 enzyme to the resin.

EXAMPLE 8

Conversion of Met-Arg-Human Proinsulin Analog (B28 Lys, B29 Pro)

A 1.0×6.0 cm bDAP 1 column, prepared as described in Example 7, was washed with at least 3 column volumes of dilute acetic acid. A 17 gm/l solution of partially purified recombinant MR-KPB-hPI was adjusted to pH 3.5 with 10% v/v hydrochloric acid solution or 10% w/v sodium hydroxide solution. 2000 ml of the MR-KPB-hPI solution was applied at room temperature (20–22° C.) at various linear flow rates (8 to 115 cm/hr). Effluent samples were collected for each flow rate after at least 2 column volumes had passed through the column. The extent of conversion of MR-KPB-hPI to KPB-hPI was monitored on a reverse phase HPLC analytical system consisting of a Dupont Zorbax® 5 micron 300 Å column (15×4.6 cm). The column was eluted with a morpholine/phosphate/OSA buffer system using an ACN gradient.

The relationship between the flow rate and yield was determined based on the averages of 6 different linear flow rates. The column performance was monitored by periodic evaluation of the yield at 76 cm/hr and was found to be between 54 and 61%.

After a 19 day storage period, a second run was made on the column by passing a 400 ml portion of MR-KPB-hPI across the column. The yield at 76 cm/hr was 55%.

45 days from the first conversion, a third run was made by passing a 600 ml portion of MR-KPB-hPI across the column. The yield at 76 cm/hr, based on 2 effluent samples, was 46–52%.

When not in use, the column was washed and stored in dilute acetic acid, pH 3.5 at room temperature (about 20° C.). During the application of MR-KPB-hPI described above, minimal decrease in percentage conversion of MR-KPB-hPI was measured.

During the conversion runs described above in Example 8, the immobilized bDAP 1 on the column was exposed to the equivalent of 7.5 standard batch-mode MR-KPB-hPI conversion reactions. This translated to a total of 3000 ml (approximately 51 gm) of MR-KPB-hPI that was converted in these experiments. In contrast, 8 units of bDAP 1 used as the free enzyme in a batch mode process would only convert 400 ml (approximately 6.8 gm) of MR-KPB-hPI in a given time window. This calculation demonstrated that the presently claimed method is more efficient than a batch mode process.

EXAMPLE 9

Conversion of Met-Arg-Human Proinsulin Analog (B28 Lys, B29 Pro) at Varying Concentrations A 1.0×6.0 cm bDAP 1 column, prepared as described in Example 7, was washed with at least 3 column volumes of dilute acetic acid. A 17 gm/l solution of partially purified recombinant MR-KPB-hPI was adjusted to pH 3.5 with 10% v/v hydrochloric acid solution or 10% w/v sodium hydroxide solution. A 17 gm/l solution of MR-KPB-hPI was diluted to about 3.4 mg/ml and 0.85 mg/ml with dilute acetic acid.

The 17 mg/ml, 3.4 mg/ml, and 0.85 mg/ml solutions of MR-KPB-hPI were applied at room temperature (20–22° C.) at various linear flow rates (115, 76, and 23 cm/hr). Effluent samples were collected for each flow rate after at least 2 column volumes had passed through the column. The extent of conversion of MR-KPB-hPI to KPB-hPI was monitored on a reverse phase HPLC analytical system consisting of a Dupont ZORBAX® 5 micron 300 Å column (15×4.6 cm). The column was eluted with a morpholine/phosphate/OSA buffer system using an ACN gradient.

The relationship between the yield and flow rate was essentially identical for each substrate concentration. (At a flow rate of 115 cm/hr, the yields for the 17, 3.4, and 0.85 gram per liter solutions were 48%, 50%, and 50% respectively. At a flow rate of 76 cm/hr, the yields for the 17, 3.4, and 0.85 mg/ml solutions were 55%, 58%, and 58% respectively. At a flow rate of 23 cm/hr, the yields for the 17, 3.4, and 0.85 mg/ml solutions were 83%, 89%, and 85% respectively.) This demonstrated that the conversion yield was not a function of substrate concentration when using a 10 U per cm² immobilized bDAP 1 column.

EXAMPLE 10

Conversion of Met-Arg-Human Proinsulin Analog (B28 Lys, B29 Pro) Using a Reslurried bDAP 1 Column The resin in the column used in Example 8 was reslurried with 1 column volume of dilute acetic acid. The column was packed and washed with at least 3 column volumes of dilute acetic acid. A 17 gm/l solution of partially purified MR-KPB-hPI was adjusted to pH 3.5 with 10% v/v hydrochloric acid solution or 10% w/v sodium hydroxide solution.

The MR-KPB-hPI solution was applied at room temperature (20–22° C.) at various linear flow rates (115, 76, 38, 23, 10, and 4 cm/hr). Effluent samples were collected for each flow rate after at least 2 column volumes had passed through the column. The extent of conversion of MR-KPB-hPI to KPB-hPI was monitored on a reverse phase HPLC analytical system consisting of a Dupont Zorbax® 5 micron 300 Å column (15×4.6 cm). The column was eluted with a morpholine/phosphate/OSA buffer system using an ACN gradient.

The relationship between the yield and flow rate was essentially identical to the yields before the reslurry. At a flow rate of 115 cm/hr, the yield was 39%, as compared to 38–41% on the column before reslurry.

EXAMPLE 11

Scaled-up Conversion of Met-Arg-Human Proinsulin Analog (B28 Lys, B29 Pro)

The 7 L (30×10 cm) immobilized bDAP 1 column prepared as described in Example 7 at 10 U per cm² was washed with at least 4 column volumes of dilute acetic acid, pH 3.5. 218 liters of a 16 gm/l solution of partially purified MR-KPB-hPI (approximately 3488 gm) was adjusted to pH 3.5 with 10% v/v hydrochloric acid solution or 10% w/v sodium hydroxide solution. The MR-KPB-hPI solution was warmed from 4° C. to 21° C., and the temperature was maintained at 21° C. during the processing time (30–35 hours). The solution was applied to the column at 10 cm/hr. Samples of the effluent and charge were taken every 2 hours to monitor the conversion reaction. After the MR-KPB-hPI solution was depleted, the column was washed with 3 column volumes of dilute acetic acid, pH 3.5 at 10 cm/hr. The first column volume was collected and stored with the KPB-hPI effluent, and the column was stored in dilute acetic acid at 21° C.

The extent of conversion of MR-KPB-hPI to KPB-hPI was monitored on a reverse phase HPLC analytical system consisting of a Dupont ZORBAX® 5 micron 300 Å column (15×4.6 cm) at 35° C. The column was eluted with an isocratic morpholine/OSA/ACN buffer system. The A buffer (25% ACN) and B buffer (50% ACN) mixture was maintained at 38–42% ACN. The conversion yield across the column averaged about 98%.

After 11 days, the column was flushed with at least 3 column volumes of dilute acetic acid at 20° C. The column flow-through was measured for bDAP 1 activity using the GFpNA activity assay. No activity was detected in the column flow-through fraction that eluted from the column, indicating no significant leaching of active bDAP 1 from the column resin.

242 liters of a 17.5 gm/l solution of partially purified MR-KPB-hPI was obtained and adjusted to pH 3.5 with 10% v/v hydrochloric acid solution or 10% w/v sodium hydroxide solution. The temperature of the MR-KPB-hPI solution was maintained at 2–4° C. during the processing time (30–35 hours). An in-line heat exchanger was used to warm the MR-KPB-hPI charge to 20–22° C. The solution was applied to the column at 10 cm/hr.

Samples of the effluent and charge were taken every 2 hours to monitor the conversion reaction. After the MR-KPB-hPI was depleted, the column was flushed with 3 column volumes of dilute acetic acid at 10 cm/hr. The first column volume was collected and stored with the KPB-hPI effluent, and the other two column volumes were collected as waste. The column was stored in dilute acetic acid at 20° C.

The extent of conversion of MR-KPB-hPI to KPB-hPI was monitored on a reverse phase HPLC analytical system consisting of a Dupont ZORBAX® C-8, 5 micron 300 Å column (15×4.6 cm) at 35° C. The column was eluted with an isocratic morpholine/OSA/ACN buffer system. The A buffer (25% ACN) and B buffer (50% ACN) mixture was maintained at 38–42% ACN. The conversion yield across the column averaged about 92%.

EXAMPLE 12

Covalent Immobilization of bDAP 1 and Its Use in Processing Met-Asp-Human Growth Hormone One gram of CH SEPHAROSE® 4B (Pharmacia) was swelled in 100 mM acetic acid, pH 5. One mL of the swelled resin was washed extensively with additional 100 mM acetic acid, pH 5. A 1:1 (v/v) slurry of resin and buffer was prepared to which 23 mU of purified bDAP 1 (prepared in accordance with Examples 1 and 2) was added. The mixture was gently mixed by inversion for about 18 hours at 4° C. The resin was then packed, at room temperature, in a 0.5×5 cm (1.0 mL) column (Pharmacia HR 5/5®) and washed down flow at 0.2 mL/min (16.7 cm/hr) with 2.0 mL of 0.5M Tris, pH 7. The Tris buffer was allowed to incubate with the resin for an additional 30 minutes to allow quenching of remaining activated sites. The column was further washed down flow with 2.0 mL of 0.05M acetic acid, pH 3.5; 2 mL of 0.5M Tris, 0.5M NaCl, pH 7; and 4.0 mL of 0.05M acetic acid, pH 3.5 to prepare and equilibrate the column for contact with precursor protein.

Met-Asp-hGH was produced as an insoluble protein in the cytoplasm of *E. coli*. The insoluble protein was solubilized, folded to produce proper disulfide-paired Met-Asp-hGH and purified by ion-exchange chromatography. This preparation was solvent exchanged and adjusted to pH 3.5 for use as the precursor protein solution for the immobilized bDAP 1 column. The absorbance of the solution at 280 nm was used to determine that the approximate concentration of Met-Asp-hGH was 5 mg/mL.

The Met-Asp-hGH precursor protein solution (5 mg) was applied to the column at a linear flow rate of 1.25 cm/hr. The column flow-through was diluted ten-fold in a solution of 100 mM Tris, 30% acetonitrile, pH 8 and assayed by reverse phase chromatography and a human growth hormone (hGH) conversion yield of 37% was determined. Further experiments showed that an additional 60 mg of Met-Asp-hGH solution could be processed over this column with an average hGH yield of 33%. Periodic sampling of the column flow-through indicated that the hGH yield was consistent throughout the run. A total of 65 mg of Met-Asp-hGH was processed.

In a batch-mode reaction, about 390 mU of bDAP 1 would be required to process 65 mg of Met-Asp-hGH. The experiment demonstrated the feasibility of using covalently immobilized bDAP 1 to process Met-Asp-hGH to hGH with a many-fold decrease in bDAP 1 use as compared to a batch-mode conversion reaction.

EXAMPLE 13

Recycle and Discrete Pass Conversions of Met-Arg-Human Proinsulin Analog (B28 Lys, B29 Pro)

A column measuring 0.5×5 cm was prepared as described in Example 7 with a level of bDAP 1 equivalent to 10 units per cm$^2$. A solution (approximately 17 g/L) of partially purified recombinant MR-KPB-hPI was adjusted to pH 3.5 with 10% v/v hydrochloric acid solution or 10% w/v sodium hydroxide solution. The MR-KPB-hPI solution was charged to the column at room temperature (20–22° C.) at 100 cm/hr. After approximately 8 column volumes, the effluent was continuously recycled back to the charge container. Samples were periodically taken from the charge container.

The extent of conversion of MR-KPB-hPI to KPB-hPI was monitored on a reverse phase HPLC analytical system consisting of a Dupont ZORBAX® 5 micron 300 A column (15×4.6 cm). The column was eluted with a morpholine/phosphate/OSA buffer system using an ACN gradient. The yield after 1, 2, and 3 pass equivalents (total volume across the column divided by the total volume of solution in the charge container and lines) was 58%, 71%, and 80% respectively.

The previously prepared column was washed with at least 3 column volumes of dilute acetic acid. The previously prepared MR-KPB-hPI solution was charged to the column at room temperature (20–22° C.) at flow rates of 150 cm/hr and 50 cm/hr. The effluent was collected and recharged across the column for 2 to 3 additional discrete passes. Effluent samples were taken after each discrete pass. The extent of conversion of MR-KPB-hPI to KPB-hPI was monitored on the previously described analytical system. The cumulative yield after each discrete pass was 59%, 81%, and 85% at 150 cm/hr; 75%, 86%, 86%, and 89% at 50 cm/hr.

This demonstrated that a desired conversion step yield can be obtained at higher linear flow rates by recycling the column effluent or by discrete passes across a single column.

EXAMPLE 14

Conversion of Met-Arg-Human Proinsulin Analog (B28 Lys, B29 Pro) using Immobilized Columns in Series Three columns measuring 0.5×4.5 cm were prepared individually as described in Example 7 with a level of bDAP 1 equivalent to 10 units per cm$^2$. The columns were connected in series and washed with at least 3 column volumes of dilute acetic acid. A solution (approximately 17 g/L) of partially purified recombinant MR-KPB-hPI was adjusted to pH 3.5 with 10% v/v hydrochloric acid solution or 10% w/v sodium hydroxide solution. The MR-KPB-hPI solution was charged to the columns at room temperature (20–22° C.) at 40–50 cm/hr.

The extent of conversion of MR-KPB-hPI to KPB-hPI was monitored on a reverse phase HPLC analytical system consisting of a Dupont ZORBAX® 5 micron 300 A column (15×4.6 cm). The column was eluted with a morpholine/phosphate/OSA buffer system using an ACN gradient. The yield ranged from 84% to 90%.

This demonstrated that a desired conversion step yield can be obtained at higher linear flow rates by utilizing multiple columns in series.

We claim:

1. An isolated nucleic acid molecule encoding bovine dipeptidylaminopeptidase 1, said nucleic acid molecule having a sequence as described in SEQ ID NO:1.

2. An isolated nucleic acid molecule as claimed in claim 1, further comprising a signal sequence operably linked thereto.

3. An isolated nucleic acid molecule as claimed in claim 2, said nucleic acid molecule and signal sequence having a sequence as described in SEQ ID NO:3.

4. An expression vector comprising a nucleic acid molecule of claim 2 operably linked to an expression control sequence.

5. A host cell transformed with a vector of claim 4.

6. A vector comprising the nucleic acid molecule of claim 1.

7. A host cell transformed with a vector of claim 6.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1317 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1317

(xi) SEQUENCE DESCRIPTION: SEQ ID NO:1:

```
GAC ACG CCT GCC AAC TGC ACC TAC CCC GAC CTG CTG GGC ACC TGG GTC      48
Asp Thr Pro Ala Asn Cys Thr Tyr Pro Asp Leu Leu Gly Thr Trp Val
 1               5                  10                  15

TTC CAG GTG GGC TCC AGC GGC TCC CAG CGC GAT GTC AAC TGC TCG GTG      96
Phe Gln Val Gly Ser Ser Gly Ser Gln Arg Asp Val Asn Cys Ser Val
                20                  25                  30

ATG GGA CCC CCA GAA AAA AAA GTG GTG GTG CAC CTC AAG AAG TTG GAT     144
Met Gly Pro Pro Glu Lys Lys Val Val Val His Leu Lys Lys Leu Asp
             35                  40                  45

ACA GCA TAT GAT GAC TTT GGC AAT TCC GGC CAT TTC ACC ATC ATT TAC     192
```

-continued

| | | | | | | | | | | | | | | |
|---|---|---|---|---|---|---|---|---|---|---|---|---|---|---|
| Thr | Ala | Tyr | Asp | Asp | Phe | Gly | Asn | Ser | Gly | His | Phe | Thr | Ile | Ile | Tyr |
| | 50 | | | | | 55 | | | | | 60 | | | | |

```
AAT CAA GGC TTT GAG ATT GTG TTG AAT GAC TAC AAG TGG TTC GCC TTT      240
Asn Gln Gly Phe Glu Ile Val Leu Asn Asp Tyr Lys Trp Phe Ala Phe
 65              70                  75                  80

TTT AAG TAT AAA GAA GAG GGT GGC AAG GTA ACC AGT TAC TGC CAC GAG      288
Phe Lys Tyr Lys Glu Glu Gly Gly Lys Val Thr Ser Tyr Cys His Glu
                 85                  90                  95

ACC ATG ACT GGC TGG GTC CAT GAC GTG CTG GGC CGG AAC TGG GCC TGT      336
Thr Met Thr Gly Trp Val His Asp Val Leu Gly Arg Asn Trp Ala Cys
                100                 105                 110

TTC ACT GGA AGG AAG ACA GGA AAT ACC TCG GAG AAC GTG AAC GTG AAC      384
Phe Thr Gly Arg Lys Thr Gly Asn Thr Ser Glu Asn Val Asn Val Asn
            115                 120                 125

ACA GCA CGC CTT GCG GGT CTC GAG GAA ACG TAT TCT AAT AGG CTC TAC      432
Thr Ala Arg Leu Ala Gly Leu Glu Glu Thr Tyr Ser Asn Arg Leu Tyr
        130                 135                 140

AGA TAT AAC CAT GAC TTT GTG AAA GCT ATC AAT GCC ATT CAG AAG TCT      480
Arg Tyr Asn His Asp Phe Val Lys Ala Ile Asn Ala Ile Gln Lys Ser
145                 150                 155                 160

TGG ACT GCA GCC CCA TAC ATG GAA TAT GAG ACT CTT ACC CTA AAA GAG      528
Trp Thr Ala Ala Pro Tyr Met Glu Tyr Glu Thr Leu Thr Leu Lys Glu
                165                 170                 175

ATG ATT AGG AGA GGT GGT GGC CAT AGC CGG AGA ATT CCA AGG CCC AAA      576
Met Ile Arg Arg Gly Gly Gly His Ser Arg Arg Ile Pro Arg Pro Lys
                180                 185                 190

CCT GCA CCA ATC ACT GCT GAA ATA CAG AAA AAG ATT TTG CAT TTG CCA      624
Pro Ala Pro Ile Thr Ala Glu Ile Gln Lys Lys Ile Leu His Leu Pro
            195                 200                 205

ACA TCC TGG GAT TGG AGA AAC GTT CAT GGT ATC AAT TTT GTT ACT CCT      672
Thr Ser Trp Asp Trp Arg Asn Val His Gly Ile Asn Phe Val Thr Pro
        210                 215                 220

GTT CGA AAC CAA GGG TCT TGT GGA AGC TGC TAC TCA TTT GCT TCT ATG      720
Val Arg Asn Gln Gly Ser Cys Gly Ser Cys Tyr Ser Phe Ala Ser Met
225                 230                 235                 240

GGG ATG ATG GAA GCA AGA ATC CGC ATA CTA ACC AAC AAC ACT CAG ACC      768
Gly Met Met Glu Ala Arg Ile Arg Ile Leu Thr Asn Asn Thr Gln Thr
                245                 250                 255

CCG ATC TTG AGT CCT CAG GAG GTT GTG TCT TGC AGT CAG TAT GCT CAA      816
Pro Ile Leu Ser Pro Gln Glu Val Val Ser Cys Ser Gln Tyr Ala Gln
                260                 265                 270

GGC TGT GAA GGT GGC TTC CCT TAC CTC ATC GCA GGG AAG TAT GCC CAG      864
Gly Cys Glu Gly Gly Phe Pro Tyr Leu Ile Ala Gly Lys Tyr Ala Gln
            275                 280                 285

GAC TTT GGG TTG GTG GAA GAG GAC TGT TTC CCC TAC ACA GGC ACG GAT      912
Asp Phe Gly Leu Val Glu Glu Asp Cys Phe Pro Tyr Thr Gly Thr Asp
        290                 295                 300

TCG CCG TGC AGA CTG AAA GAG GGC TGC TTC CGG TAC TAT TCC TCC GAG      960
Ser Pro Cys Arg Leu Lys Glu Gly Cys Phe Arg Tyr Tyr Ser Ser Glu
305                 310                 315                 320

TAC CAC TAC GTG GGC GGT TTC TAC GGG GGC TGC AAT GAA GCC CTG ATG     1008
Tyr His Tyr Val Gly Gly Phe Tyr Gly Gly Cys Asn Glu Ala Leu Met
                325                 330                 335

AAG CTT GAG CTG GTC CAT CAG GGG CCC ATG GCC GTC GCC TTT GAA GTC     1056
Lys Leu Glu Leu Val His Gln Gly Pro Met Ala Val Ala Phe Glu Val
                340                 345                 350

TAC GAC GAC TTC CTC CAC TAC CGC AAG GGC GTC TAC CAC CAC ACG GGG     1104
Tyr Asp Asp Phe Leu His Tyr Arg Lys Gly Val Tyr His His Thr Gly
            355                 360                 365

CTG CGA GAC CCT TTC AAC CCC TTC GAG CTG ACC AAT CAT GCT GTG CTG     1152
```

```
Leu Arg Asp Pro Phe Asn Pro Phe Glu Leu Thr Asn His Ala Val Leu
    370                 375                 380

CTG GTG GGC TAT GGC ACT GAC GCG GCC TCT GGA CTG GAT TAC TGG ATT        1200
Leu Val Gly Tyr Gly Thr Asp Ala Ala Ser Gly Leu Asp Tyr Trp Ile
385                 390                 395                 400

GTT AAA AAC AGC TGG GGC ACC AGC TGG GGT GAG AAC GGT TAC TTC CGC        1248
Val Lys Asn Ser Trp Gly Thr Ser Trp Gly Glu Asn Gly Tyr Phe Arg
                405                 410                 415

ATC CGC AGA GGA ACC GAC GAG TGT GCG ATC GAA AGC ATA GCG CTG GCG        1296
Ile Arg Arg Gly Thr Asp Glu Cys Ala Ile Glu Ser Ile Ala Leu Ala
                420                 425                 430

GCC ACC CCG ATT CCT AAG TTG                                             1317
Ala Thr Pro Ile Pro Lys Leu
                435
```

(2) INFORMATION FOR SEQ ID NO:2:

(i) SEQUENCE CHARACTERISTICS:
        (A) LENGTH: 439 amino acids
        (B) TYPE: amino acid
        (D) TOPOLOGY: linear (ii) MOLECULE TYPE: protein (xi) SEQUENCE DESCRIPTION: SEQ ID NO:2:

```
Asp Thr Pro Ala Asn Cys Thr Tyr Pro Asp Leu Leu Gly Thr Trp Val
1               5                   10                  15

Phe Gln Val Gly Ser Ser Gly Ser Gln Arg Asp Val Asn Cys Ser Val
                20                  25                  30

Met Gly Pro Pro Glu Lys Lys Val Val His Leu Lys Lys Leu Asp
            35                  40                  45

Thr Ala Tyr Asp Asp Phe Gly Asn Ser Gly His Phe Thr Ile Ile Tyr
        50                  55                  60

Asn Gln Gly Phe Glu Ile Val Leu Asn Asp Tyr Lys Trp Phe Ala Phe
65                  70                  75                  80

Phe Lys Tyr Lys Glu Glu Gly Gly Lys Val Thr Ser Tyr Cys His Glu
                85                  90                  95

Thr Met Thr Gly Trp Val His Asp Val Leu Gly Arg Asn Trp Ala Cys
            100                 105                 110

Phe Thr Gly Arg Lys Thr Gly Asn Thr Ser Glu Asn Val Asn Val Asn
        115                 120                 125

Thr Ala Arg Leu Ala Gly Leu Glu Glu Thr Tyr Ser Asn Arg Leu Tyr
    130                 135                 140

Arg Tyr Asn His Asp Phe Val Lys Ala Ile Asn Ala Ile Gln Lys Ser
145                 150                 155                 160

Trp Thr Ala Ala Pro Tyr Met Glu Tyr Glu Thr Leu Thr Leu Lys Glu
                165                 170                 175

Met Ile Arg Arg Gly Gly His Ser Arg Arg Ile Pro Arg Pro Lys
            180                 185                 190

Pro Ala Pro Ile Thr Ala Glu Ile Gln Lys Lys Ile Leu His Leu Pro
        195                 200                 205

Thr Ser Trp Asp Trp Arg Asn Val His Gly Ile Asn Phe Val Thr Pro
    210                 215                 220

Val Arg Asn Gln Gly Ser Cys Gly Ser Cys Tyr Ser Phe Ala Ser Met
225                 230                 235                 240

Gly Met Met Glu Ala Arg Ile Arg Ile Leu Thr Asn Asn Thr Gln Thr
                245                 250                 255

Pro Ile Leu Ser Pro Gln Glu Val Val Ser Cys Ser Gln Tyr Ala Gln
```

```
                           260                 265                 270
           Gly Cys Glu Gly Gly Phe Pro Tyr Leu Ile Ala Gly Lys Tyr Ala Gln
                       275                 280                 285

Asp Phe Gly Leu Val Glu Glu Asp Cys Phe Pro Tyr Thr Gly Thr Asp
                   290                 295                 300

Ser Pro Cys Arg Leu Lys Glu Gly Cys Phe Arg Tyr Tyr Ser Ser Glu
           305                 310                 315                 320

Tyr His Tyr Val Gly Gly Phe Tyr Gly Gly Cys Asn Glu Ala Leu Met
                               325                 330                 335

Lys Leu Glu Leu Val His Gln Gly Pro Met Ala Val Ala Phe Glu Val
                           340                 345                 350

Tyr Asp Asp Phe Leu His Tyr Arg Lys Gly Val Tyr His His Thr Gly
                       355                 360                 365

Leu Arg Asp Pro Phe Asn Pro Phe Glu Leu Thr Asn His Ala Val Leu
                   370                 375                 380

Leu Val Gly Tyr Gly Thr Asp Ala Ala Ser Gly Leu Asp Tyr Trp Ile
           385                 390                 395                 400

Val Lys Asn Ser Trp Gly Thr Ser Trp Gly Glu Asn Gly Tyr Phe Arg
                               405                 410                 415

Ile Arg Arg Gly Thr Asp Glu Cys Ala Ile Glu Ser Ile Ala Leu Ala
                           420                 425                 430

Ala Thr Pro Ile Pro Lys Leu
                       435

(2) INFORMATION FOR SEQ ID NO:3:

(i) SEQUENCE CHARACTERISTICS:
        (A) LENGTH: 1392 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1389

(xi) SEQUENCE DESCRIPTION: SEQ ID NO:3:

ATG GGT CCC TGG TCC GGC TCG CGG CTC GTC GCT CTC TTG CTG CTC GTC        48
Met Gly Pro Trp Ser Gly Ser Arg Leu Val Ala Leu Leu Leu Leu Val
 1               5                  10                  15

TAT GGC GCT GGC TCC GTG CGC GGG GAC ACG CCT GCC AAC TGC ACC TAC        96
Tyr Gly Ala Gly Ser Val Arg Gly Asp Thr Pro Ala Asn Cys Thr Tyr
             20                  25                  30

CCC GAC CTG CTG GGC ACC TGG GTC TTC CAG GTG GGC TCC AGC GGC TCC       144
Pro Asp Leu Leu Gly Thr Trp Val Phe Gln Val Gly Ser Ser Gly Ser
         35                  40                  45

CAG CGC GAT GTC AAC TGC TCG GTG ATG GGA CCC CCA GAA AAA AAA GTG       192
Gln Arg Asp Val Asn Cys Ser Val Met Gly Pro Pro Glu Lys Lys Val
     50                  55                  60

GTG GTG CAC CTC AAG AAG TTG GAT ACA GCA TAT GAT GAC TTT GGC AAT       240
Val Val His Leu Lys Lys Leu Asp Thr Ala Tyr Asp Asp Phe Gly Asn
 65                  70                  75                  80

TCC GGC CAT TTC ACC ATC ATT TAC AAT CAA GGC TTT GAG ATT GTG TTG       288
Ser Gly His Phe Thr Ile Ile Tyr Asn Gln Gly Phe Glu Ile Val Leu
                 85                  90                  95

AAT GAC TAC AAG TGG TTC GCC TTT TTT AAG TAT AAA GAA GAG GGT GGC       336
Asn Asp Tyr Lys Trp Phe Ala Phe Phe Lys Tyr Lys Glu Glu Gly Gly
            100                 105                 110
```

| | |
|---|---|
| AAG GTA ACC AGT TAC TGC CAC GAG ACC ATG ACT GGC TGG GTC CAT GAC<br>Lys Val Thr Ser Tyr Cys His Glu Thr Met Thr Gly Trp Val His Asp<br>115                    120                    125 | 384 |
| GTG CTG GGC CGG AAC TGG GCC TGT TTC ACT GGA AGG AAG ACA GGA AAT<br>Val Leu Gly Arg Asn Trp Ala Cys Phe Thr Gly Arg Lys Thr Gly Asn<br>130                    135                    140 | 432 |
| ACC TCG GAG AAC GTG AAC GTG AAC ACA GCA CGC CTT GCG GGT CTC GAG<br>Thr Ser Glu Asn Val Asn Val Asn Thr Ala Arg Leu Ala Gly Leu Glu<br>145                150                    155                    160 | 480 |
| GAA ACG TAT TCT AAT AGG CTC TAC AGA TAT AAC CAT GAC TTT GTG AAA<br>Glu Thr Tyr Ser Asn Arg Leu Tyr Arg Tyr Asn His Asp Phe Val Lys<br>                  165                    170                    175 | 528 |
| GCT ATC AAT GCC ATT CAG AAG TCT TGG ACT GCA GCC CCA TAC ATG GAA<br>Ala Ile Asn Ala Ile Gln Lys Ser Trp Thr Ala Ala Pro Tyr Met Glu<br>                  180                    185                    190 | 576 |
| TAT GAG ACT CTT ACC CTA AAA GAG ATG ATT AGG AGA GGT GGT GGC CAT<br>Tyr Glu Thr Leu Thr Leu Lys Glu Met Ile Arg Arg Gly Gly Gly His<br>                195                    200                    205 | 624 |
| AGC CGG AGA ATT CCA AGG CCC AAA CCT GCA CCA ATC ACT GCT GAA ATA<br>Ser Arg Arg Ile Pro Arg Pro Lys Pro Ala Pro Ile Thr Ala Glu Ile<br>210                    215                    220 | 672 |
| CAG AAA AAG ATT TTG CAT TTG CCA ACA TCC TGG GAT TGG AGA AAC GTT<br>Gln Lys Lys Ile Leu His Leu Pro Thr Ser Trp Asp Trp Arg Asn Val<br>225                    230                    235                    240 | 720 |
| CAT GGT ATC AAT TTT GTT ACT CCT GTT CGA AAC CAA GGG TCT TGT GGA<br>His Gly Ile Asn Phe Val Thr Pro Val Arg Asn Gln Gly Ser Cys Gly<br>                  245                    250                    255 | 768 |
| AGC TGC TAC TCA TTT GCT TCT ATG GGG ATG ATG GAA GCA AGA ATC CGC<br>Ser Cys Tyr Ser Phe Ala Ser Met Gly Met Met Glu Ala Arg Ile Arg<br>                  260                    265                    270 | 816 |
| ATA CTA ACC AAC AAC ACT CAG ACC CCG ATC TTG AGT CCT CAG GAG GTT<br>Ile Leu Thr Asn Asn Thr Gln Thr Pro Ile Leu Ser Pro Gln Glu Val<br>                275                    280                    285 | 864 |
| GTG TCT TGC AGT CAG TAT GCT CAA GGC TGT GAA GGT GGC TTC CCT TAC<br>Val Ser Cys Ser Gln Tyr Ala Gln Gly Cys Glu Gly Gly Phe Pro Tyr<br>290                    295                    300 | 912 |
| CTC ATC GCA GGG AAG TAT GCC CAG GAC TTT GGG TTG GTG GAA GAG GAC<br>Leu Ile Ala Gly Lys Tyr Ala Gln Asp Phe Gly Leu Val Glu Glu Asp<br>305                    310                    315                    320 | 960 |
| TGT TTC CCC TAC ACA GGC ACG GAT TCG CCG TGC AGA CTG AAA GAG GGC<br>Cys Phe Pro Tyr Thr Gly Thr Asp Ser Pro Cys Arg Leu Lys Glu Gly<br>                  325                    330                    335 | 1008 |
| TGC TTC CGG TAC TAT TCC TCC GAG TAC CAC TAC GTG GGC GGT TTC TAC<br>Cys Phe Arg Tyr Tyr Ser Ser Glu Tyr His Tyr Val Gly Gly Phe Tyr<br>                  340                    345                    350 | 1056 |
| GGG GGC TGC AAT GAA GCC CTG ATG AAG CTT GAG CTG GTC CAT CAG GGG<br>Gly Gly Cys Asn Glu Ala Leu Met Lys Leu Glu Leu Val His Gln Gly<br>                355                    360                    365 | 1104 |
| CCC ATG GCC GTC GCC TTT GAA GTC TAC GAC GAC TTC CTC CAC TAC CGC<br>Pro Met Ala Val Ala Phe Glu Val Tyr Asp Asp Phe Leu His Tyr Arg<br>370                    375                    380 | 1152 |
| AAG GGC GTC TAC CAC CAC ACG GGG CTG CGA GAC CCT TTC AAC CCC TTC<br>Lys Gly Val Tyr His His Thr Gly Leu Arg Asp Pro Phe Asn Pro Phe<br>385                    390                    395                    400 | 1200 |
| GAG CTG ACC AAT CAT GCT GTG CTG CTG GTG GGC TAT GGC ACT GAC GCG<br>Glu Leu Thr Asn His Ala Val Leu Leu Val Gly Tyr Gly Thr Asp Ala<br>                  405                    410                    415 | 1248 |
| GCC TCT GGA CTG GAT TAC TGG ATT GTT AAA AAC AGC TGG GGC ACC AGC<br>Ala Ser Gly Leu Asp Tyr Trp Ile Val Lys Asn Ser Trp Gly Thr Ser<br>                420                    425                    430 | 1296 |

```
TGG GGT GAG AAC GGT TAC TTC CGC ATC CGC AGA GGA ACC GAC GAG TGT      1344
Trp Gly Glu Asn Gly Tyr Phe Arg Ile Arg Arg Gly Thr Asp Glu Cys
        435                 440                 445

GCG ATC GAA AGC ATA GCG CTG GCG GCC ACC CCG ATT CCT AAG TTG          1389
Ala Ile Glu Ser Ile Ala Leu Ala Ala Thr Pro Ile Pro Lys Leu
450                 455                 460

TAG                                                                   1392

(2) INFORMATION FOR SEQ ID NO:4:

(i) SEQUENCE CHARACTERISTICS:
        (A) LENGTH: 463 amino acids
        (B) TYPE: amino acid
        (D) TOPOLOGY: linear (ii) MOLECULE TYPE: protein (xi) SEQUENCE DESCRIPTION: SEQ ID NO:4:
```

Met Gly Pro Trp Ser Gly Ser Arg Leu Val Ala Leu Leu Leu Val
 1               5                  10                  15

Tyr Gly Ala Gly Ser Val Arg Gly Asp Thr Pro Ala Asn Cys Thr Tyr
                20                  25                  30

Pro Asp Leu Leu Gly Thr Trp Val Phe Gln Val Gly Ser Ser Gly Ser
            35                  40                  45

Gln Arg Asp Val Asn Cys Ser Val Met Gly Pro Glu Lys Lys Val
50                  55                  60

Val Val His Leu Lys Lys Leu Asp Thr Ala Tyr Asp Asp Phe Gly Asn
65                  70                  75                  80

Ser Gly His Phe Thr Ile Ile Tyr Asn Gln Gly Phe Glu Ile Val Leu
                85                  90                  95

Asn Asp Tyr Lys Trp Phe Ala Phe Phe Lys Tyr Lys Glu Glu Gly Gly
                100                 105                 110

Lys Val Thr Ser Tyr Cys His Glu Thr Met Thr Gly Trp Val His Asp
            115                 120                 125

Val Leu Gly Arg Asn Trp Ala Cys Phe Thr Gly Arg Lys Thr Gly Asn
130                 135                 140

Thr Ser Glu Asn Val Asn Val Asn Thr Ala Arg Leu Ala Gly Leu Glu
145                 150                 155                 160

Glu Thr Tyr Ser Asn Arg Leu Tyr Arg Tyr Asn His Asp Phe Val Lys
                165                 170                 175

Ala Ile Asn Ala Ile Gln Lys Ser Trp Thr Ala Ala Pro Tyr Met Glu
            180                 185                 190

Tyr Glu Thr Leu Thr Leu Lys Glu Met Ile Arg Arg Gly Gly His
            195                 200                 205

Ser Arg Arg Ile Pro Arg Pro Lys Pro Ala Pro Ile Thr Ala Glu Ile
    210                 215                 220

Gln Lys Lys Ile Leu His Leu Pro Thr Ser Trp Asp Trp Arg Asn Val
225                 230                 235                 240

His Gly Ile Asn Phe Val Thr Pro Val Arg Asn Gln Gly Ser Cys Gly
                245                 250                 255

Ser Cys Tyr Ser Phe Ala Ser Met Gly Met Met Glu Ala Arg Ile Arg
            260                 265                 270

Ile Leu Thr Asn Asn Thr Gln Thr Pro Ile Leu Ser Pro Gln Glu Val
        275                 280                 285

Val Ser Cys Ser Gln Tyr Ala Gln Gly Cys Glu Gly Gly Phe Pro Tyr
290                 295                 300

Leu Ile Ala Gly Lys Tyr Ala Gln Asp Phe Gly Leu Val Glu Glu Asp

```
305                 310                 315                 320
Cys Phe Pro Tyr Thr Gly Thr Asp Ser Pro Cys Arg Leu Lys Glu Gly
                325                 330                 335
Cys Phe Arg Tyr Tyr Ser Ser Glu Tyr His Tyr Val Gly Gly Phe Tyr
                340                 345                 350
Gly Gly Cys Asn Glu Ala Leu Met Lys Leu Glu Leu Val His Gln Gly
                355                 360                 365
Pro Met Ala Val Ala Phe Glu Val Tyr Asp Asp Phe Leu His Tyr Arg
    370                 375                 380
Lys Gly Val Tyr His His Thr Gly Leu Arg Asp Pro Phe Asn Pro Phe
385                 390                 395                 400
Glu Leu Thr Asn His Ala Val Leu Leu Val Gly Tyr Gly Thr Asp Ala
                405                 410                 415
Ala Ser Gly Leu Asp Tyr Trp Ile Val Lys Asn Ser Trp Gly Thr Ser
                420                 425                 430
Trp Gly Glu Asn Gly Tyr Phe Arg Ile Arg Arg Gly Thr Asp Glu Cys
                435                 440                 445
Ala Ile Glu Ser Ile Ala Leu Ala Ala Thr Pro Ile Pro Lys Leu
    450                 455                 460
```

(2) INFORMATION FOR SEQ ID NO:5:

(i) SEQUENCE CHARACTERISTICS:
        (A) LENGTH: 1317 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:5:

```
GACACGCCUG CCAACUGCAC CUACCCCGAC CUGCUGGGCA CCUGGUCUUU CCAGGUGGGC        60
UCCAGCGGCU CCCAGCGCGA UGUCAACUGC UCGGUGAUGG ACCCCCAGA  AAAAAAAGUG       120
GUGGUGCACC UCAAGAAGUU GGAUACAGCA UAUGAUGACU UGGCAAUUC  CGGCCAUUUC       180
ACCAUCAUUU ACAAUCAAGG CUUUGAGAUU GUGUUGAAUG ACUACAAGUG GUUCGCCUUU       240
UUUAAGUAUA AAGAAGAGGG UGGCAAGGUA ACCAGUUACU GCCACGAGAC CAUGACUGGC       300
UGGGUCCAUG ACGUGCUGGG CCGGAACUGG GCCUGUUUCA CUGGAAGGAA GACAGGAAAU       360
ACCUCGGAGA ACGUGAACGU GAACACAGCA CGCCUUGCGG GUCUCGAGGA AACGUAUUCU       420
AAUAGGCUCU ACAGAUAUAA CCAUGACUUU GUGAAAGCUA UCAAUGCCAU UCAGAAGUCU       480
UGGACUGCAG CCCCAUACAU GGAAUAUGAG ACUCUUACCC UAAAAGAGAU GAUUAGGAGA       540
GGUGGUGGCC AUAGCCGGAG AAUUCCAAGG CCCAAACCUG CACCAAUCAC UGCUGAAAUA       600
CAGAAAAAGA UUUUGCAUUU GCCAACAUCC UGGGAUUGGA GAAACGUUCA UGGUAUCAAU       660
UUUGUUACUC CUGUUCGAAA CCAAGGGUCU UGUGGAAGCU GCUACUCAUU UGCUUCUAUG       720
GGGAUGAUGG AAGCAAGAAU CCGCAUACUA ACCAACAACA CUCAGACCCC GAUCUUGAGU       780
CCUCAGGAGG UUGUGUCUUG CAGUCAGUAU GCUCAAGGCU GUGAAGGUGG CUUCCCUUAC       840
CUCAUCGCAG GAAGUAUGC  CCAGGACUUU GGGUUGGUGG AAGAGGACUG UUUCCCCUAC       900
ACAGGCACGG AUUCGCCGUG CAGACUGAAA GAGGGCUGCU UCCGGUACUA UUCCUCCGAG       960
UACCACUACG UGGGCGGUUU CUACGGGGGC UGCAAUGAAG CCCUGAUGAA GCUUGAGCUG      1020
GUCCAUCAGG GGCCCAUGGC CGUCGCCUUU GAAGUCUACG ACGACUUCCU CCACUACCGC      1080
AAGGGCGUCU ACCACCACAC GGGGCUGCGA GACCCUUUCA ACCCCUUCGA GCUGACCAAU      1140
```

```
CAUGCUGUGC UGCUGGUGGG CUAUGGCACU GACGCGGCCU CUGGACUGGA UUACUGGAUU      1200

GUUAAAAACA GCUGGGGCAC CAGCUGGGGU GAGAACGGUU ACUUCCGCAU CCGCAGAGGA      1260

ACCGACGAGU GUGCGAUCGA AAGCAUAGCG CUGGCGGCCA CCCCGAUUCC UAAGUUG         1317

(2) INFORMATION FOR SEQ ID NO:6:

(i) SEQUENCE CHARACTERISTICS:
        (A) LENGTH: 1392 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:6:

AUGGGUCCCU GGUCCGGCUC GCGGCUCGUC GCUCUCUUGC UGCUCGUCUA UGGCGCUGGC        60

UCCGUGCGCG GGGACACGCC UGCCAACUGC ACCUACCCCG ACCUGCUGGG CACCUGGGUC       120

UUCCAGGUGG GCUCCAGCGG CUCCCAGCGC GAUGUCAACU GCUCGGUGAU GGGACCCCCA       180

GAAAAAAAG UGGUGGUGCA CCUCAAGAAG UUGGAUACAG CAUAUGAUGA CUUUGGCAAU        240

UCCGGCCAUU UCACCAUCAU UUACAAUCAA GGCUUUGAGA UUGUGUUGAA UGACUACAAG       300

UGGUUCGCCU UUUUUAAGUA UAAAGAAGAG GGUGGCAAGG UAACCAGUUA CUGCCACGAG       360

ACCAUGACUG GCUGGGUCCA UGACGUGCUG GGCCGGAACU GGGCCUGUUU CACUGGAAGG       420

AAGACAGGAA AUACCUCGGA GAACGUGAAC GUGAACACAG CACGCCUUGC GGGUCUCGAG       480

GAAACGUAUU CUAAUAGGCU CUACAGAUAU AACCAUGACU UGUGAAAGC UAUCAAUGCC        540

AUUCAGAAGU CUUGGACUGC AGCCCCAUAC AUGGAAUAUG AGACUCUUAC CCUAAAAGAG       600

AUGAUUAGGA GAGGUGGUGG CCAUAGCCGG AGAAUUCCAA GGCCCAAACC UGCACCAAUC       660

ACUGCUGAAA UACAGAAAAA GAUUUUGCAU UUGCCAACAU CCUGGGAUUG GAGAAACGUU       720

CAUGGUAUCA AUUUUGUUAC UCCUGUUCGA AACCAAGGGU CUUGUGGAAG CUGCUACUCA       780

UUUGCUUCUA UGGGGAUGAU GGAAGCAAGA AUCCGCAUAC UAACCAACAA CACUCAGACC       840

CCGAUCUUGA GUCCUCAGGA GGUUGUGUCU UGCAGUCAGU AUGCUCAAGG CUGUGAAGGU       900

GGCUUCCCUU ACCUCAUCGC AGGGAAGUAU GCCCAGGACU UUGGGUUGGU GGAAGAGGAC       960

UGUUUCCCCU ACACAGGCAC GGAUUCGCCG UGCAGACUGA AAGAGGGCUG CUUCCGGUAC      1020

UAUUCCUCCG AGUACCACUA CGUGGGCGGU UUCUACGGGG GCUGCAAUGA AGCCCUGAUG      1080

AAGCUUGAGC UGGUCCAUCA GGGGCCCAUG GCCGUCGCCU UUGAAGUCUA CGACGACUUC      1140

CUCCACUACC GCAAGGGCGU CUACCACCAC ACGGGGCUGC GAGACCCUUU CAACCCCUUC      1200

GAGCUGACCA AUCAUGCUGU GCUGCUGGUG GCUAUGGCA CUGACGCGGC CUCUGGACUG       1260

GAUUACUGGA UUGUUAAAAA CAGCUGGGGC ACCAGCUGGG GUGAGAACGG UUACUUCCGC      1320

AUCCGCAGAG GAACCGACGA GUGUGCGAUC GAAAGCAUAG CGCUGGCGGC CACCCCGAUU      1380

CCUAAGUUGU AG                                                         1392
```